(12) United States Patent
Bertinetti et al.

(10) Patent No.: US 7,942,380 B2
(45) Date of Patent: May 17, 2011

(54) PORTABLE POSITIVE AIRWAY PRESSURE DEVICE ACCESSORIES AND METHODS FOR USE THEREOF

(75) Inventors: Mark Bertinetti, Lane Cove (AU); Philip James Jenkinson, Chittaway Point (AU); Geoffrey Daniel Daly, Sherwood (AU)

(73) Assignee: ResMed Limited, Bella Vista (AU)

( * ) Notice: Subject to any disclaimer, the term of this patent is extended or adjusted under 35 U.S.C. 154(b) by 1002 days.

(21) Appl. No.: 11/808,454

(22) Filed: Jun. 11, 2007

(65) Prior Publication Data

US 2007/0299358 A1 Dec. 27, 2007

Related U.S. Application Data

(60) Provisional application No. 60/812,081, filed on Jun. 9, 2006.

(51) Int. Cl.
*F16M 11/00* (2006.01)
(52) U.S. Cl. ..................................................... 248/682
(58) Field of Classification Search .................. 248/682, 248/688, 689, 51, 52; 600/529
See application file for complete search history.

(56) References Cited

U.S. PATENT DOCUMENTS

| 5,821,458 A * | 10/1998 | Wenzel ........................ 174/651 |
| 6,336,454 B1 | 1/2002 | Farrell et al. |
| D486,916 S | 2/2004 | Cheung et al. |
| 2003/0230701 A1* | 12/2003 | Chang ........................... 248/682 |
| 2004/0194210 A1 | 10/2004 | Foster et al. |
| 2010/0001155 A1* | 1/2010 | Grundy et al. ............ 248/231.81 |

FOREIGN PATENT DOCUMENTS

| DE | 103 23 754 A1 | 12/2004 |
| WO | WO 02/66106 | 2/2002 |
| WO | WO 02/066107 A1 | 8/2002 |

OTHER PUBLICATIONS

French Search Report mailed Mar. 7, 2011 for corresponding French Application No. 0704142, 5 pages.

\* cited by examiner

*Primary Examiner* — Ramon O Ramirez
(74) *Attorney, Agent, or Firm* — Nixon & Vanderhye P.C.

(57) ABSTRACT

A portable cradle for carrying a PAP device includes a base and a handle that is provided on the base. The base is structured to receive the PAP device and attachments to the PAP device. The base is oriented in a substantially horizontal position when the handle is lifted. A trolley may be provided to easily wheel the PAP device and store multiple accessories. Detachable battery packs may also be provided for attachment to a cradle.

30 Claims, 25 Drawing Sheets

PORTABLE POSITIVE AIRWAY PRESSURE DEVICE ACCESSORIES AND METHODS FOR USE THEREOF

This application claims the benefit of U.S. Provisional Application No. 60/812,081, filed on Jun. 9, 2006.

BACKGROUND OF THE INVENTION

1. Field of the Invention

The present invention relates to a portable breathing apparatus, and more particularly, to a portable cradle for carrying a positive airway pressure (PAP) device, also known as a flow generator.

2. Description of Related Art

Sleep-disorders are fairly common. Millions of people suffer from some form of sleep disorder, including insomnia, narcolepsy, and sleep apnea. The most common sleep apnea form occurs when an obstruction blocks or partially blocks the upper airway of a person's respiratory system. Such an obstruction may cause a person to stop breathing temporarily, which often causes snoring.

Treatment for sleep apnea can take many forms, including the use of a breathing apparatus. A typical breathing apparatus includes a flow generator, or blower, also known as a positive airway pressure (PAP) device that generates airflow, and a mask through which the air flows to a person's nose and/or mouth. Different types of systems are used to treat specific disorders. For example, a first type of PAP device provides continuous positive airway pressure ("CPAP") to ensure the person's airway stays open while the person is sleeping. A second type of PAP device is an auto titration device that adjusts the positive air pressure as a person's needs change during the sleep cycle. A third type of PAP device, typically referred to as a bi-level device, provides continuous pressure at two distinct levels of pressure. A higher pressure is delivered when the person inhales and a lower pressure is delivered when the person exhales. The bi-level device is used for a broader range of respiratory treatments, not just sleep apneas.

Although most PAP devices, regardless of type, are fairly compact and can be moved by the user from location to location, they are not truly portable because they are typically required to be connected to an electrical outlet. Also, most PAP devices require two hands to carry them, which make them unsuitable to be easily carried around.

It is common for patients requiring IVs in hospitals to use a portable stand so that intravenous fluids can still be administered while the patient exercises or moves from place to place within the hospital. However, when a person is in a hospital and requires treatment with a breathing apparatus that includes a PAP device, the lack of system portability prevents the patient from being moved around the hospital by hospital personnel. Therefore, it would be advantageous for the patient that is being treated with a breathing apparatus to be able to use some type of truly portable breathing apparatus so that the patient is not forced to be confined to one room.

Such a portable system would optionally include battery power so that an electrical cord is not needed. This adds weight to the system and can make the PAP device more difficult to carry. Therefore, there is a need for a device that allows the PAP device to be easily carried and also allows a battery to be carried along with the PAP device, as well as any additional accessories that may be needed for proper diagnosis and treatment.

Another drawback in the art relates to storage of a range of nasal CPAP devices. The healthcare systems in many countries, particularly the U.S., require patients to attend a sleep lab for sleep disorder diagnosis to obtain a prescription and consequently receive a nasal CPAP device. Commonly, patients who have been prescribed a nasal CPAP device take the prescription to a local home medical equipment (HME) company who supplies them with the appropriate device. The HME company will consequently be reimbursed by a healthcare organization according to various schedules. With the increasing number of different mechanical ventilator devices, the sleep labs have to store a large range of devices. In sleep labs, any spare space is allocated for additional sleep assessment rooms. Therefore, the storage of a range of devices for testing purposes can take up a significant amount of space.

Also, some sleep labs are now providing a complete service in which they perform the sleep assessment and then immediately supply the patients with the appropriate nasal CPAP device. Consequently, with this complete service, there is the added problem of storage space to store a range of nasal CPAP devices.

SUMMARY OF THE INVENTION

It is therefore an aspect of the present invention to provide a cradle that allows for convenient portability of a PAP device and its attachments.

Another aspect of the present invention is directed to a portable cradle for carrying a PAP device of a breathing apparatus, the cradle including a base structured to receive the PAP device on a first side and a handle provided on the base. When the handle is lifted, the base is oriented in a substantially horizontal position.

Another aspect of the present invention relates to a portable cradle for carrying a breathing apparatus PAP device and battery module. The cradle includes a base structured to receive the battery module and a handle provided on the base. The PAP device is attached to the battery module on a side opposite the base.

Yet another aspect of the present invention is directed to a portable breathing apparatus assembly including a PAP device and a cradle structured to receive the PAP device. The cradle includes a handle. When the handle is lifted, the PAP device is oriented in a substantially horizontal position.

Yet another aspect of the present invention relates to a method for providing a portable breathing apparatus that includes a PAP device and a battery module. The method includes providing a cradle to the battery module by connecting a first at least one engageable member of the cradle with at least one engageable member of the battery module, and providing the PAP device to the cradle by connecting at least one engageable member of the PAP device with a second at least one engageable member of the cradle.

Yet another aspect of the present invention relates to an air delivery system including a controllable PAP device, a controller, and a display screen. The controllable PAP device is operable to generate a supply of pressurized breathable gas to be provided to a patient for treatment. The PAP device is adapted to be operable in a plurality of delivery modes. The controller is configured to operate the PAP device in a selected one of the plurality of delivery modes. The display screen is configured to display output received from one or more patient monitoring sensors applied to the patient.

Yet another aspect of the present invention relates to a trolley including a wheel base, a support pole provided to the wheel base, a handle provided to a free end of the support pole, and one or more storage shelves or bins provided along the support pole. In one embodiment, the trolley may also provide storage for one or more oxygen cylinders. According to a further embodiment, the trolley may allow for external humidifier attachment. The trolley may also include an extendable arm to hold a mask and tubing for attachment to a PAP device.

Still another aspect of the present invention relates to a method for providing non-invasive positive pressure ventilation (NIPPV) therapy to a patient. The method includes introducing the patient to a NIPPV device having an assigned configuration at a first location (e.g., a hospital), relocating the patient from the first location to a second location, transferring the NIPPV device having the assigned configuration along with the patient to the second location, and applying NIPPV therapy to the patient with the NIPPV device while relocating the patient from the first location to the second location.

Still another aspect of the present invention relates to a method for optimizing NIPPV device management. The method includes assigning a NIPPV device to a patient in a hospital or sleep clinic setting, and providing said NIPPV device to the patient for use in a home setting.

Still another aspect of the present invention is to provide a mechanical ventilation device or PAP device that provides a range of pressure delivery modes to enable a single device to treat numerous conditions.

A further aspect of the present invention relates to a portable cradle for carrying a PAP device and at least one rechargeable battery. This embodiment includes a cradle with a base adapted to receive at least one interchangeable, rechargeable battery. According to one embodiment, the cradle receives at least two rechargeable batteries, and the batteries are hot-swappable, that is, one can power the PAP device while the other is swapped for a different one.

Yet another aspect of the present invention is directed at a battery module, adapted for connection to a portable cradle for carrying a PAP device. The battery module is provided with at least one engaging member which is communicable with the cradle. According to one embodiment, the battery module is also provided with at least one handle. According to another embodiment, the battery module is further provided with a power & communication connector having a protective lid. The protective lid may be spring loaded to slide into place over the connector when the battery is disengaged from the cradle.

Still another aspect of the present invention is directed at a portable cradle for carrying a PAP device, adapted for connection to a battery module having at least one engaging member. The portable cradle is provided with at least as many receiving holes as the battery module has engaging members, and the holes are provided on one cradle face. The cradle may be further provided with a locking plate to lock the engaging members of the battery module in place in the cradle once the battery module has been engaged with the cradle. Additionally, the cradle is provided with a locking plate release handle, adapted to release the battery module engaging members from the locking plate.

According to yet another aspect of the present invention, a portable cradle for carrying a PAP device is provided for reception of a battery module disposed between an upper side of a cradle base and a lower side of the PAP device.

A further aspect of the present invention is directed at a portable cradle for carrying a PAP device adapted for interconnection with a battery module and provided with at least one engaging member which is capable of engaging at least one engagement tab provided on a PAP device face. According to one embodiment, the cradle is also provided with a locking pin, adapted to lock into a receiving portion of a PAP device face. This pin may be released from its locking position by use of a button provided on the portable cradle.

Yet another aspect of the present invention is directed at a PAP device adapted for portable cradle interconnection. The PAP device is provided with at least one engagement tab capable of engaging at least one cradle engaging member. The tab is provided on a cradle face of the PAP device. According to one embodiment, a receiving portion capable of receiving a locking pin is also provided on a cradle face.

A further aspect of the present invention is directed at a portable cradle provided with an electrical and communications receptor for a PAP device. According to one embodiment, the electrical and communications receptor is provided on a cradle handle and is adapted for connection with an electrical and communications connector.

Another aspect of the present invention is directed at a display screen provided with an arm and an electrical and communications connector. According to one embodiment, the electrical and communications connector is provided at one end of the arm, and the other end of the arm is affixed to a display screen. The electrical and communications connector is adapted for connection with an electrical and communications receptor.

Yet another aspect of the present invention is directed at a remote adapter provided with an electrical and communications receptor. The remote adapter allows display screen use with a PAP device in the absence of a cradle. According to one embodiment, the adapter is provided with a cord adapted for PAP device connection. The electrical and communications receptor of the adapter is also adapted to connect to an electrical and communications connector, such as an electrical and communications connector provided on the arm of a display screen. Additionally, the adapter may be provided with rubber feet on a bottom surface, to aid in stability of the attached screen. Alternatively, the adapter may be wall mounted or attached to any other surface.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

1. Portable Cradle

Figure 1:
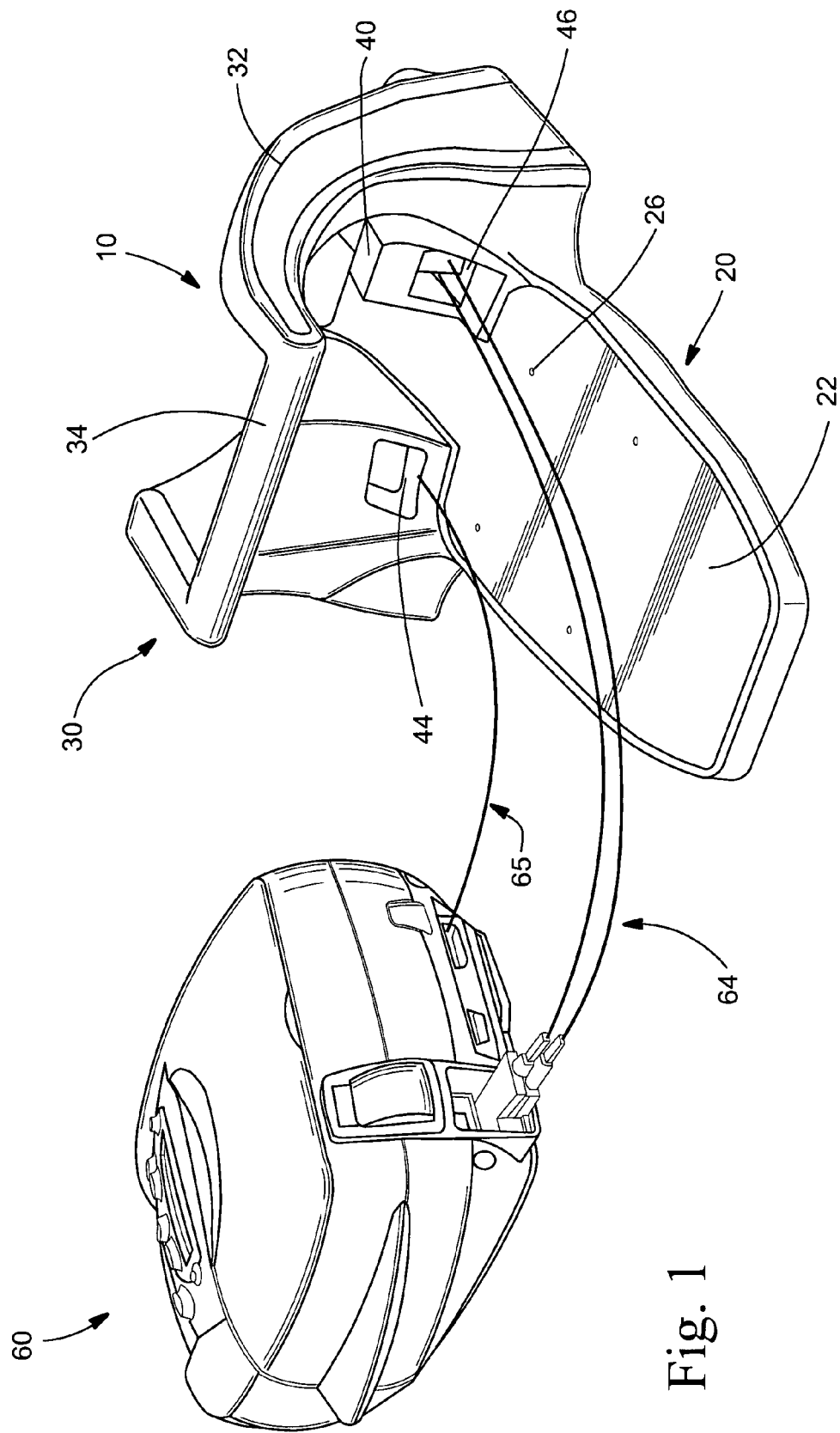
FIG. 1 is a front perspective view of a portable cradle according to an embodiment of the present invention in its unloaded state and a rear perspective view of a PAP device.

FIG. 1 shows a portable cradle 10 for carrying an apparatus that enhances breathing and a PAP device 60, which is part of the breathing apparatus. As shown in FIG. 1, the cradle 10 includes a base 20 and a handle 30 that is provided on the base 20.

Figure 2:
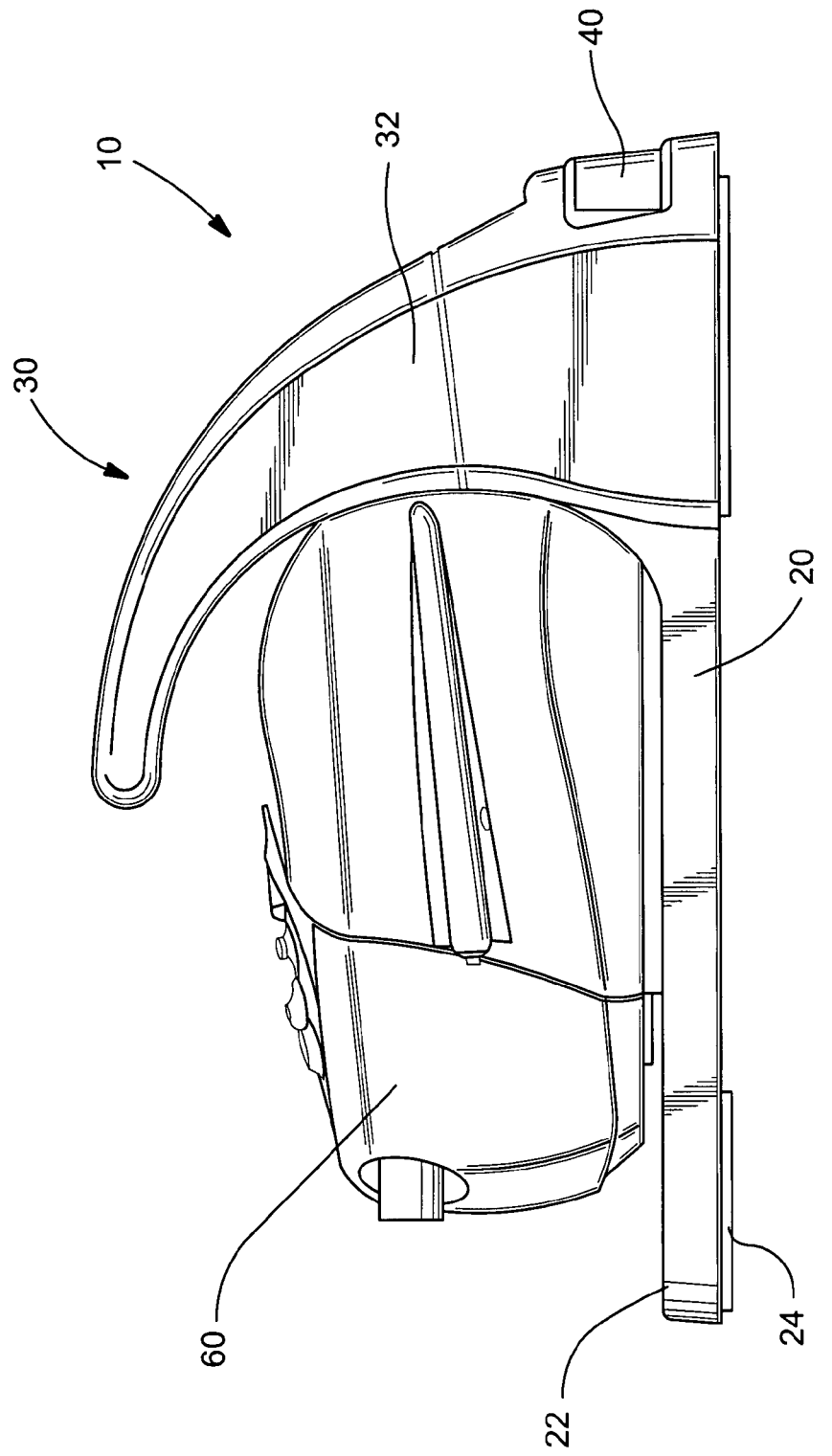
FIG. 2 is a side view of the portable cradle and PAP device of FIG. 1 in the loaded state.

In the illustrated embodiment, the base 20 is a substantially flat, elongated member that includes a first side 22 and a second side 24, as shown in FIG. 2. When the cradle 10 is sitting on a supporting surface in its normal position, as illustrated in, for example, FIG. 2, the base 20 is preferably oriented in a substantially horizontal position with the first side 22 oriented upward and the second side 24 oriented downward. Thus, the second side 24 preferably corresponds to the side of the base 20 that is in contact with the supporting surface when the cradle 10 is not being carried.

1.1 PAP Device Support

As shown in FIGS. 2-5, the base 20 is structured to receive the PAP device 60 on the first side 22. Any shape is contemplated so long as the overall dimensions of the base 20 are suitable to adequately support at least the PAP device 60. The base 20 may be substantially solid, or the base 20 may be substantially hollow. It is also contemplated that the base 20 may further include reinforcing ribs for added strength. For example, the second side 24 may include at least one reinforcing rib that extends downward, away from the first side 22 when the cradle 10 is resting in its normal position on a supporting surface.

FIG. 1 illustrates that the first side 22 of the base 20 includes at least one engageable member 26. In an embodiment, the at least one engageable member 26 is complementary in design to at least one engageable member located on a bottom side of the PAP device 60, such that the cradle 10 and the PAP device 60 form an interlocked structure when connected. This allows the PAP device 60 to be indexed to the correct position on the base 20 and secured into place such that it becomes attached to the cradle 10.

For example, the engageable member 26 located on the first side 22 of the base 20 may include a protrusion and the engageable member located on the bottom of the PAP device 60 may include depression or some type of slot-like configuration that complements the protrusion. It is also contemplated that the PAP device 60 may include a protrusion and the first side 22 of the base may include a complementary depression. Any type of design that will allow the PAP device 60 to be secured to the cradle 10 is contemplated. It is preferable that the PAP device 60 becomes secured to the cradle 10 in such a manner that the PAP device 60 remains attached to the cradle 10 even when the cradle 10 is oriented to a non-horizontal position. However, the engageable members 26 may be designed such that the PAP device 60 is also easily and selectively releasable from the cradle 10, if desired.

In an alternative embodiment, not illustrated, the cradle 10 may include a strap to accommodate PAP devices that are not specifically designed to be accommodated by a particular cradle. This way, if the PAP device does not have an engageable member located on its bottom side, the PAP device may still be secured to the cradle.

1.2 Handle

Figure 3:
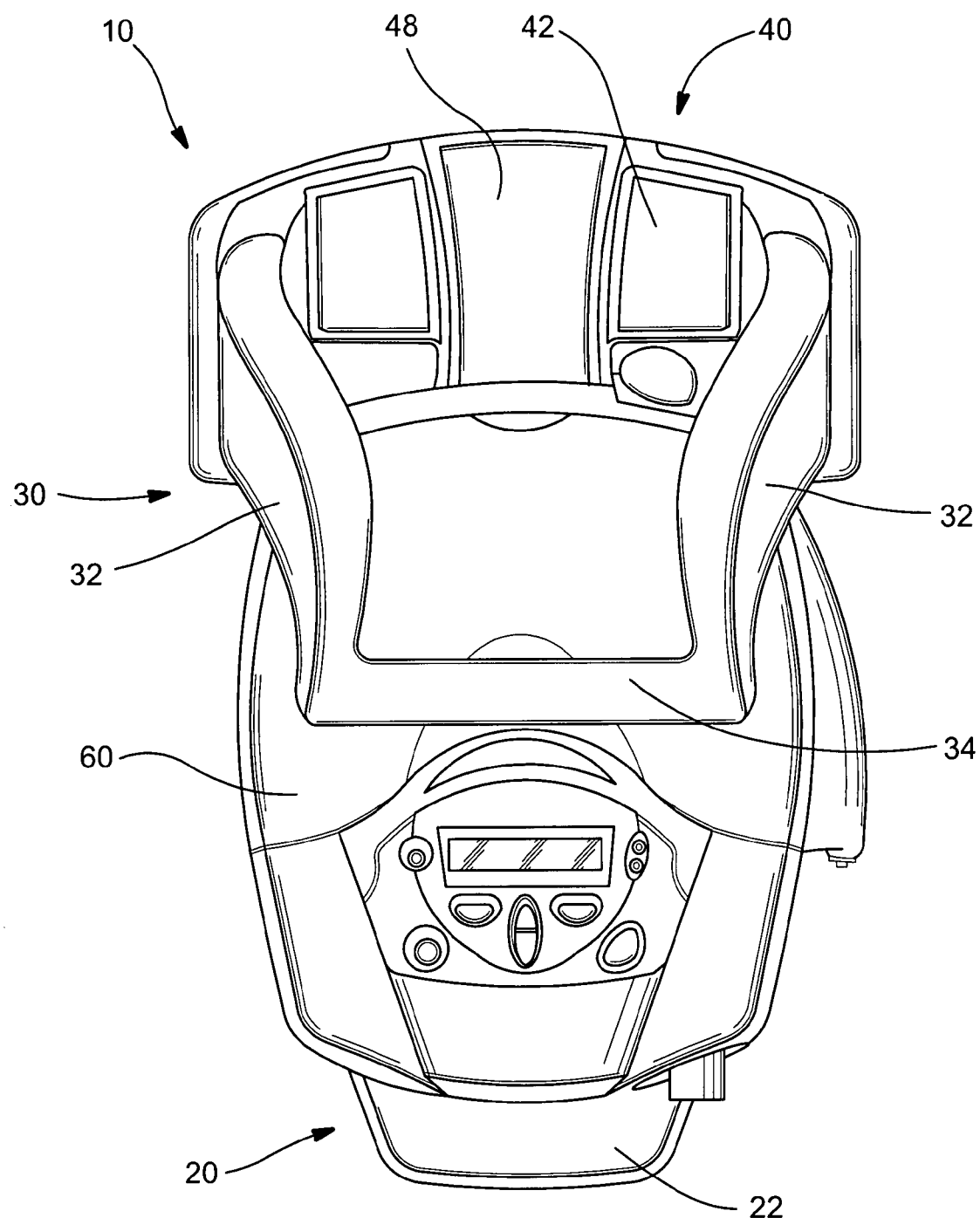
FIG. 3 is a top view of the portable cradle and PAP device of FIG. 2.

In the illustrated embodiment, the handle 30 is provided on the base 20. As illustrated, the handle 30 includes at least one arm 32 and at least one carrying portion 34. In an embodiment, the at least one arm 32 is a pair of arms 32, as illustrated in FIG. 3. The pair of arms 32 may provide additional strength and stability to the cradle 10, as compared to an embodiment that includes only one arm. In the illustrated embodiment, the pair of arms 32 are directly attached to the base 20 and extend upwardly, away from the first side 22 of the base 20 such that the arms 32 do not interfere with the positioning of any component to be supported by the cradle 10. In the illustrated embodiment, the carrying portion 34 is disposed in between the arms 32, substantially parallel to the base 20. The arms 32 may provide protection for an oxygen blender provided to the PAP device, e.g., see oxygen blender 80 in FIGS. 6-10.

The carrying portion 34 of the handle 30 is preferably sized and shaped such that a person's hand of ordinary size can fully grasp the handle 30 and the person can lift and carry the cradle 10 in a comfortable manner, even when the cradle 10 is fully loaded with the PAP device 60 and its attachments. The carrying portion 34 may be specifically located to provide balance to the cradle 10 when the PAP device 60 and its attachments are loaded on the cradle 10. Specifically, when the breathing apparatus is being carried, it may be desirable to have the PAP device 60 in a substantially horizontal orientation. Therefore, in an embodiment, the carrying portion 34 of the handle 30 is located in the same vertical plane as the center of gravity of the breathing apparatus when it is on the cradle 10, or the handle 30 is in the same vertical plane as the center of gravity for the combined cradle 10 and PAP device 60 (and any associated componentry thereof).

In an embodiment, the cross-sectional shape of the carrying portion 34 of the handle 30 is substantially round. The handle 30 may be substantially solid or may be hollow. The handle 30 preferably includes enough structure to fully support the weight of the PAP device and its attachments without failing.

It is also contemplated that the handle may be provided on the PAP device. The handle may be integrally formed on the PAP device such that it always remains on the PAP device and the PAP device remains balanced in a substantially horizontal orientation when the handle is lifted. Also, the handle may be removably attached to the PAP device such that it is possible to disconnect the handle without damaging the PAP device.

It is further contemplated that the handle may comprise a single protrusion positioned over the PAP device. This protrusion may include at least one arm with a carrying portion, and could be disposed to align with the lengthwise axis of the PAP device. This would provide a grip aligned perpendicular on a vertical plane to the grip 34 shown in FIG. 1.

1.3 Body Portion

Figure 4:
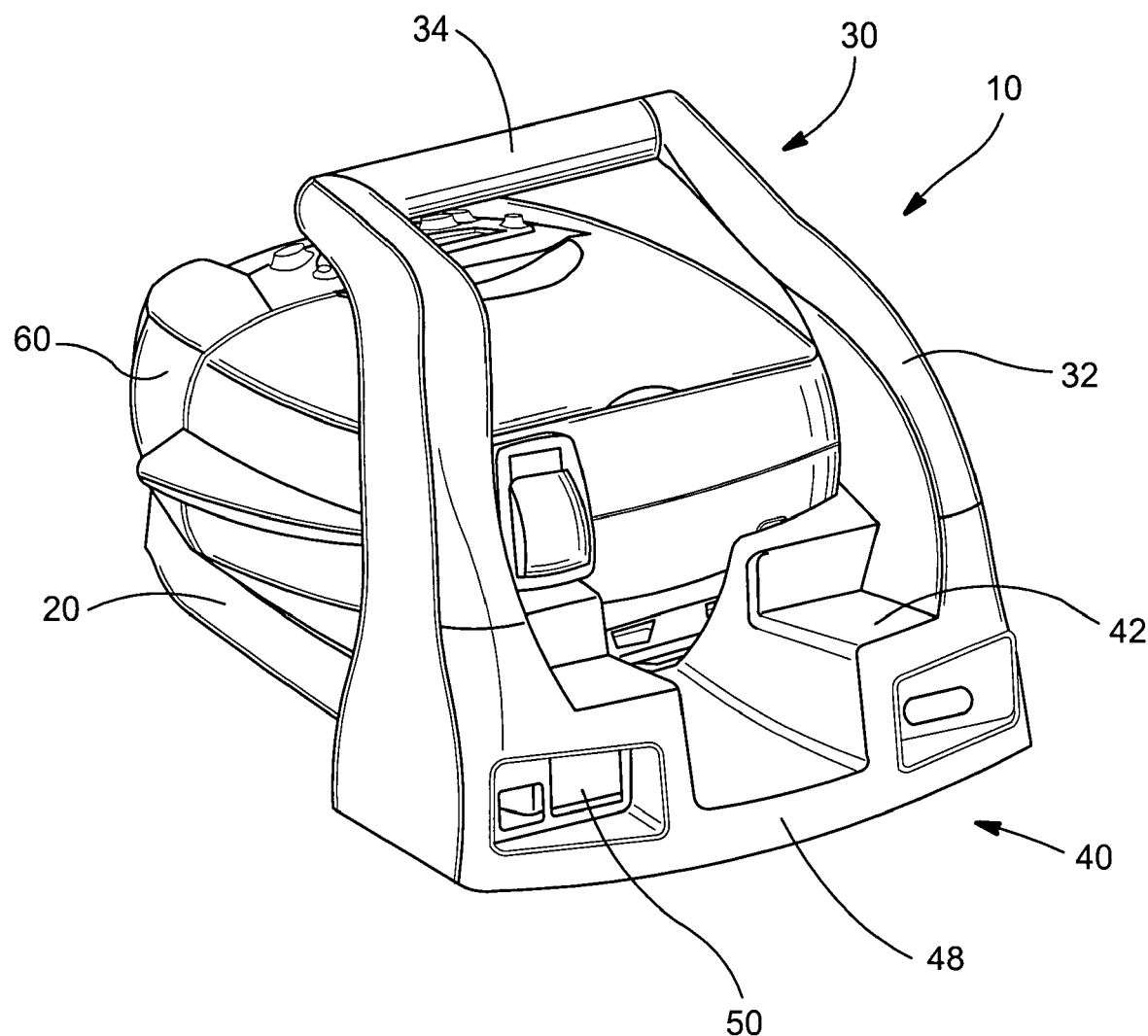
FIG. 4 is a rear perspective view of the portable cradle and PAP device of FIG. 2.
Figure 5:
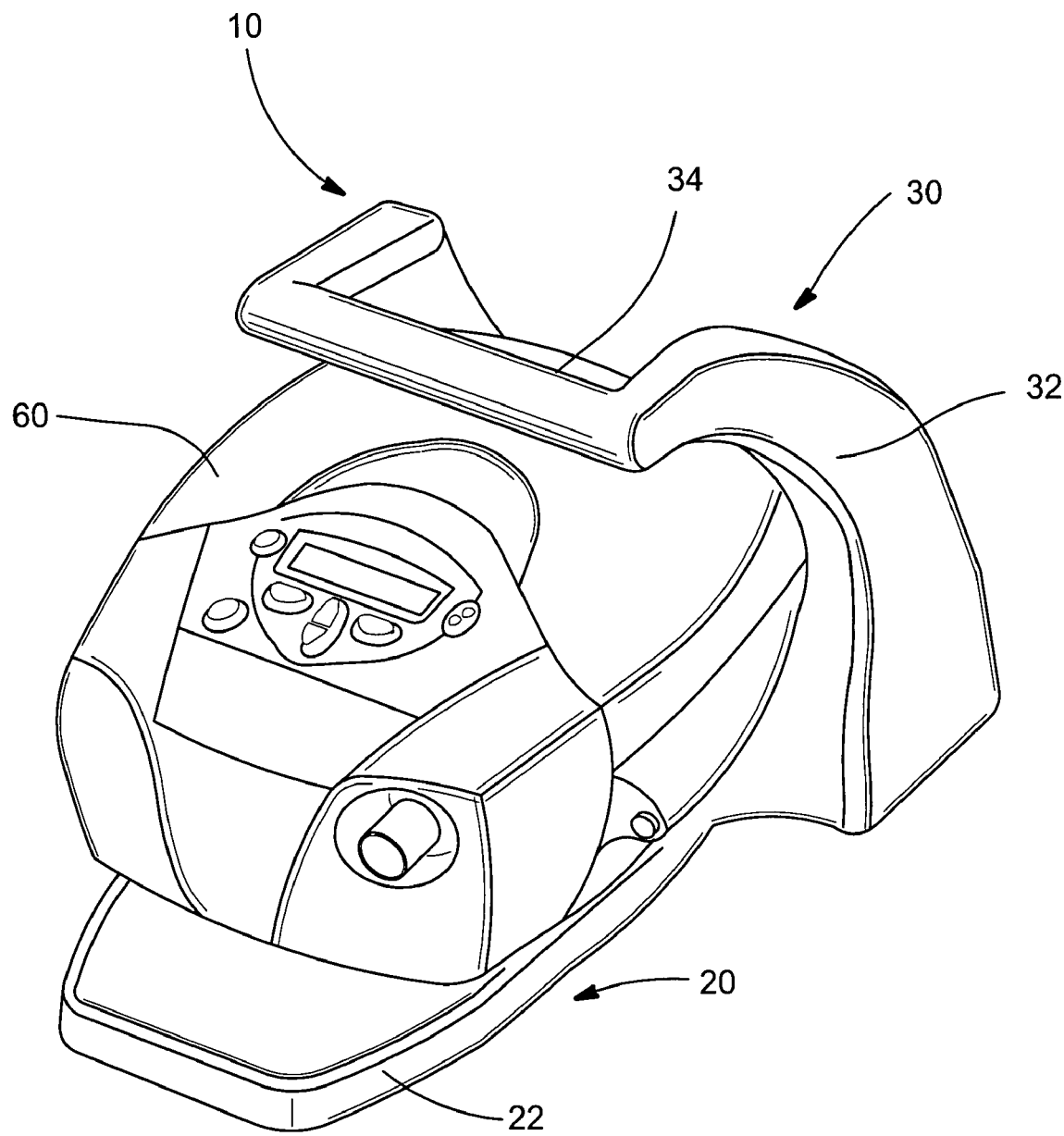
FIG. 5 is a front perspective view of the portable cradle and the PAP device of FIG. 2.

In the illustrated embodiment, as shown in, for example, FIGS. 1, 3 and 4, the cradle 10 further includes a body portion 40 that is disposed at one end of the first side 22 of the base 20. As illustrated, the body portion 40 extends upward from the base 20 and is structured to complement the design of the PAP device 60 and provide at least one attachment to the PAP device 60. For example, the body portion 40 may be contoured such that the PAP device 60 can fit snugly against the body portion 40 and may contain depressions to complement any protrusions located on the PAP device 60. In the illustrated embodiment, the body portion 40 is disposed in between the pair of arms 32 of the handle 30.

Figure 6:
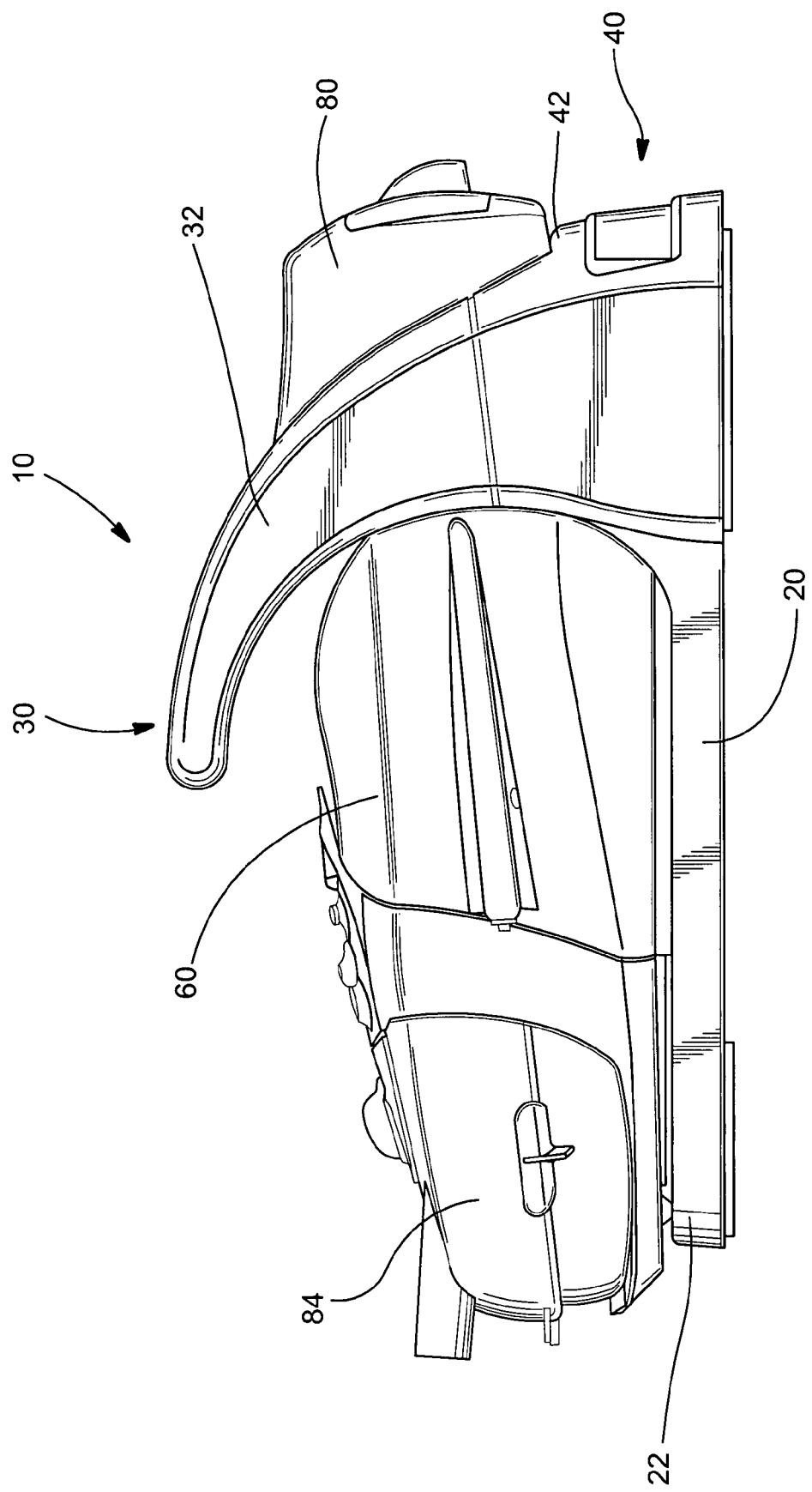
FIG. 6 is a side view of the portable cradle and PAP device of FIG. 2, with an oxygen blender and a humidifier attached to the PAP device.

The base 20 may also be structured to receive additional accessories for the PAP device 60. FIG. 6 shows a humidifier 84 that is supported by the first side 22 of the base 20 and attached to the PAP device 60. The humidifier 84 provides moisture to the air that exits the PAP device 60. Details of the humidifier 84 are disclosed in PCT application numbers PCT/AU02/00155 and PCT/AU02/00156, filed Feb. 14, 2002, each of which is incorporated herein by reference in its entirety.

1.4 Battery Module

Figure 7:
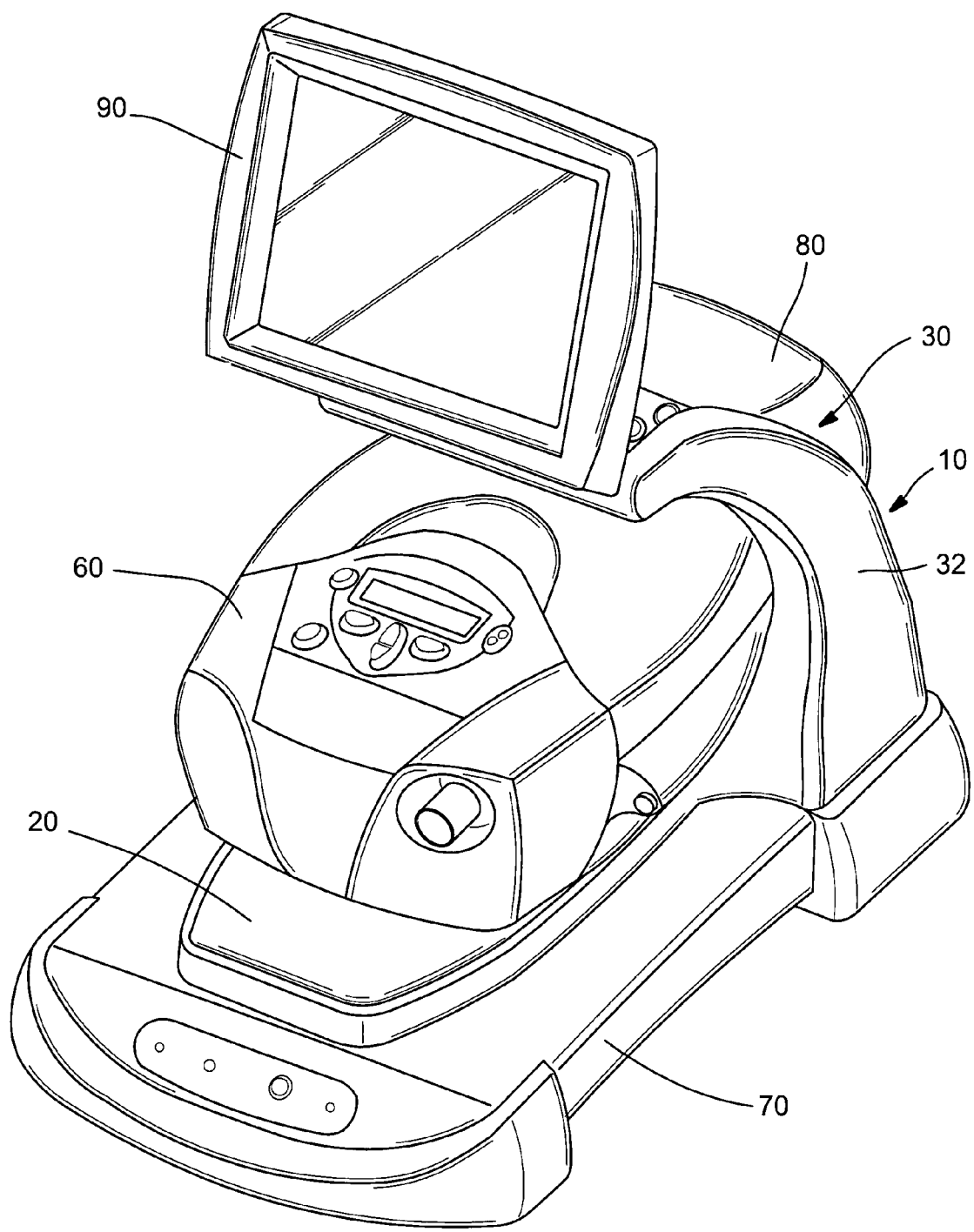
FIG. 7 is a front perspective view of the portable cradle and PAP device of FIG. 5 with a battery module and data screen attached to the cradle and an oxygen blender attached to the PAP device.

FIG. 7 shows a battery module 70 that may be used to power the PAP device 60. The second side 24 of the base 20 may include at least one engageable member. In one embodiment, the at least one engageable member is complementary in design to at least one engageable member located on the top side of the battery module 70, such that the cradle 10 and the battery module 70 form an interlocked structure. This allows the battery module 70 to be indexed to the correct position on the base 20 and secured into place such that it becomes attached to the cradle 10.

For example, the engageable member may be one part of a slot-like configuration or of any type of design that will allow the battery module 70 to be secured to the cradle 10. It is also contemplated that the second side 24 of the base 20 may include slots or depressions that are complementary in design to any protrusions located on the mating surface of the battery module 70, such that the cradle 10 is received by the battery module 70. This arrangement avoids protrusions on the second side 24 which may affect balance when the cradle 10 is not attached to the battery module 70. However, the second side 24 of the base 20 may include protrusions, and the mating surface of the battery module 70 may include slots. In one embodiment, the cradle 10 fully supports the weight of the battery module 70, such that the battery module 70 does not fall off of the cradle 10 when the cradle 10 is lifted away from a supporting surface or is oriented in a non-horizontal position.

In an alternative embodiment, not illustrated, the battery module 70 may attach to the cradle 10 on the first side 22 of the base 20 in a similar manner. In this embodiment, the PAP device 60 attaches directly to the battery module 70, rather than the arrangement described above where the base 20 is positioned in between the PAP device 60 and the battery module 70. In such an arrangement, the PAP device 60 does not attach directly to the first side 22 of the base 20 but instead attaches to the battery module 70 and the battery module 70 attaches to the first side 22 of the base with the use of the engageable members described above.

1.5 Data Screen

Figure 8:
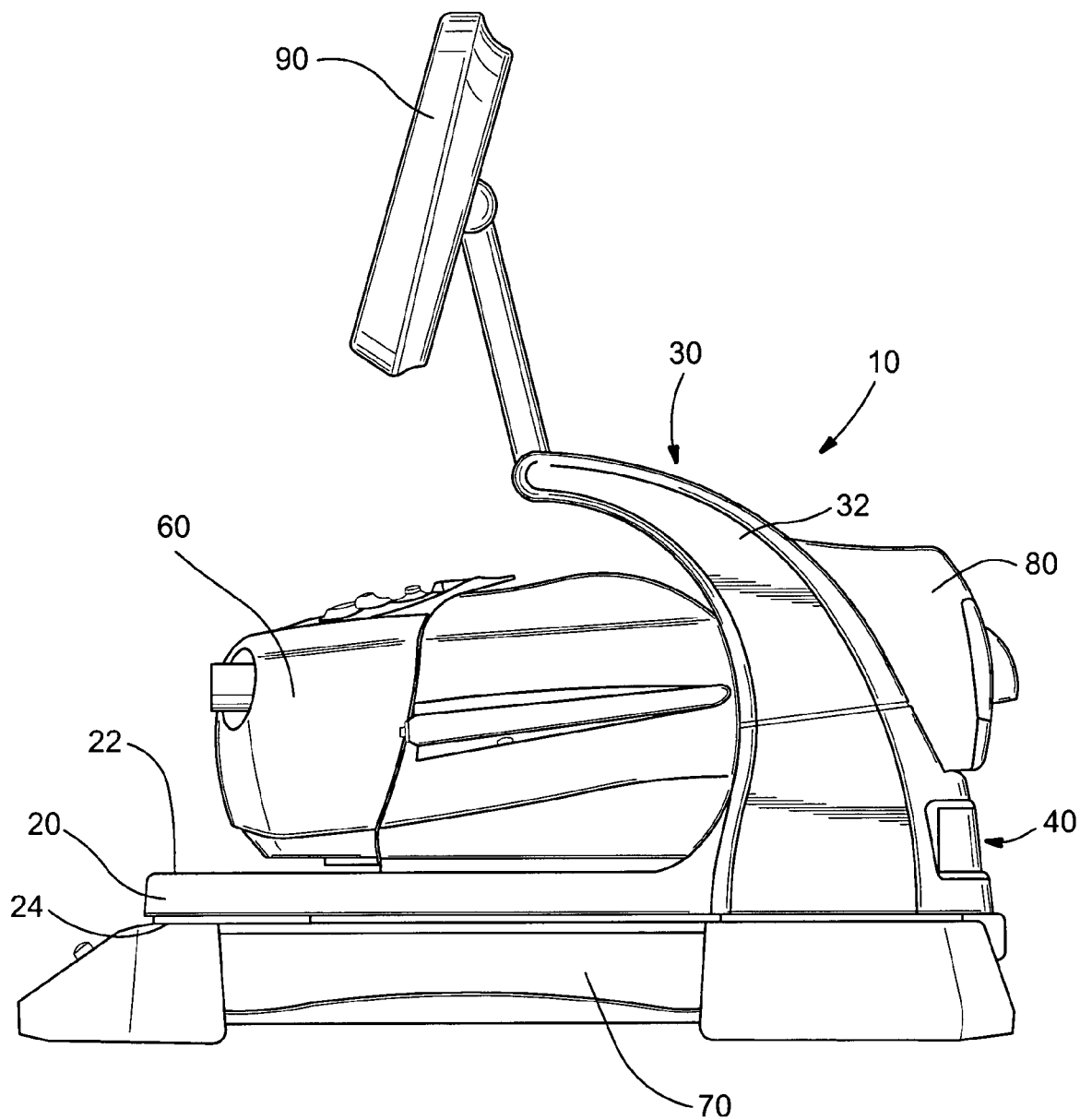
FIG. 8 is a side view of the portable cradle, PAP device, battery module, data screen, and oxygen blender of FIG. 7.
Figure 9:
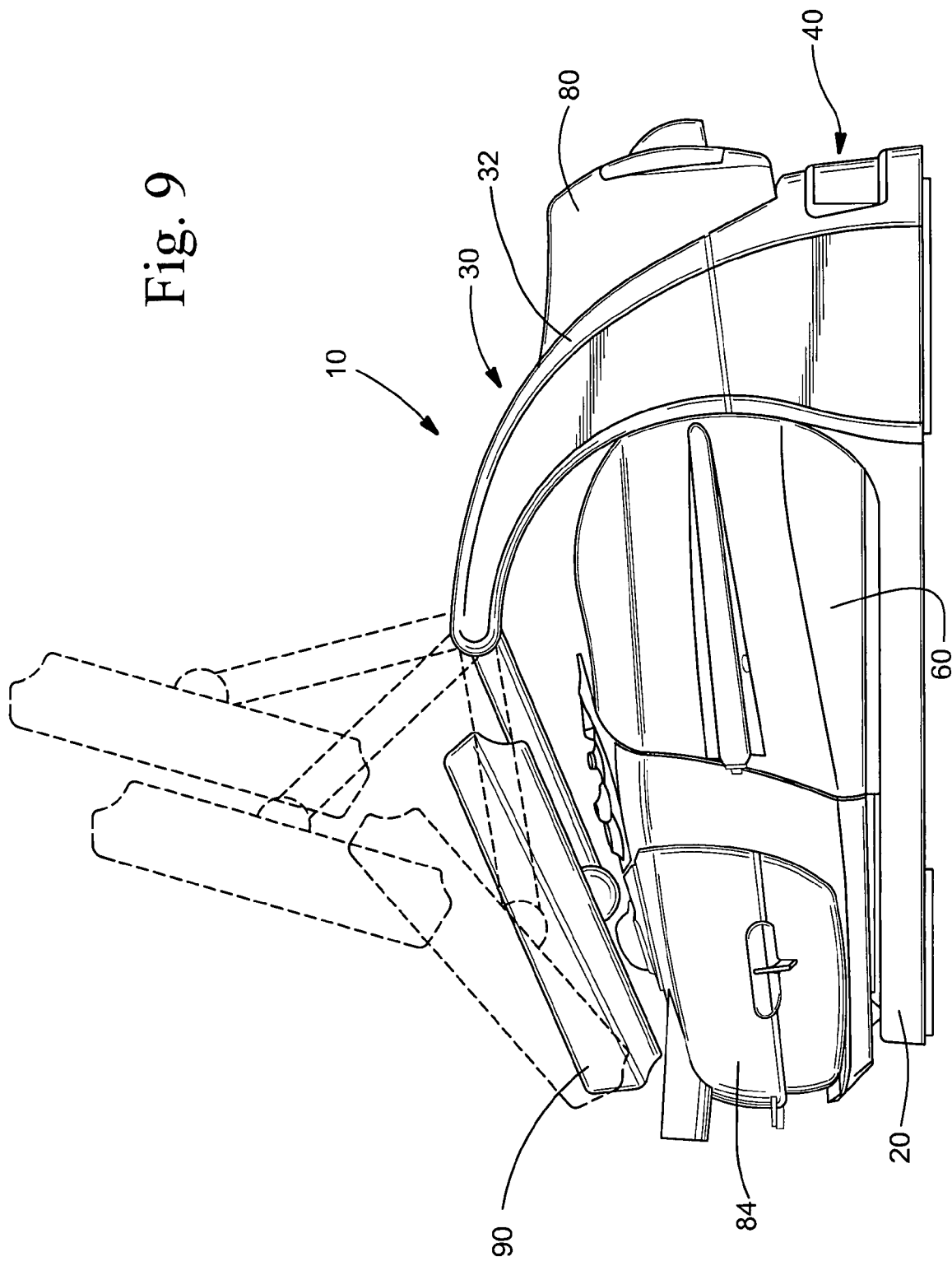
FIG. 9 is a side view of the portable cradle, PAP device, oxygen blender, and humidifier of FIG. 6 with a data screen shown in varying positions.

In an embodiment, the handle 30 includes a space that is sized large enough to allow communication cords, or wiring, to be contained within the handle 30. This not only allows for storage of the communications cords, but allows for the attachment of accessories directly to the handle 30. For example, as shown in FIGS. 7 and 8, the carrying portion 34 of the handle 30 may be structured to receive a rod or a tube that is connected to an accessory such as a monitor or data screen 90. The data screen 90 could then be rotated to any number of positions, as shown in FIG. 9. The appropriate communications cords, such as data cords and power cords, may be routed from the base 20 of the cradle 10 through the arms 32 of the handle 30 such that the appropriate connection points can be made to the accessory. According to a further embodiment, the screen can be rotated at least 180 degrees, allowing the screen to be stored face down against the PAP device when not in use, or stored face up against the PAP device so the screen can be read while the cradle is in transit and the screen is in a lowered, stored position.

1.6 Accessory Support

Figure 10:
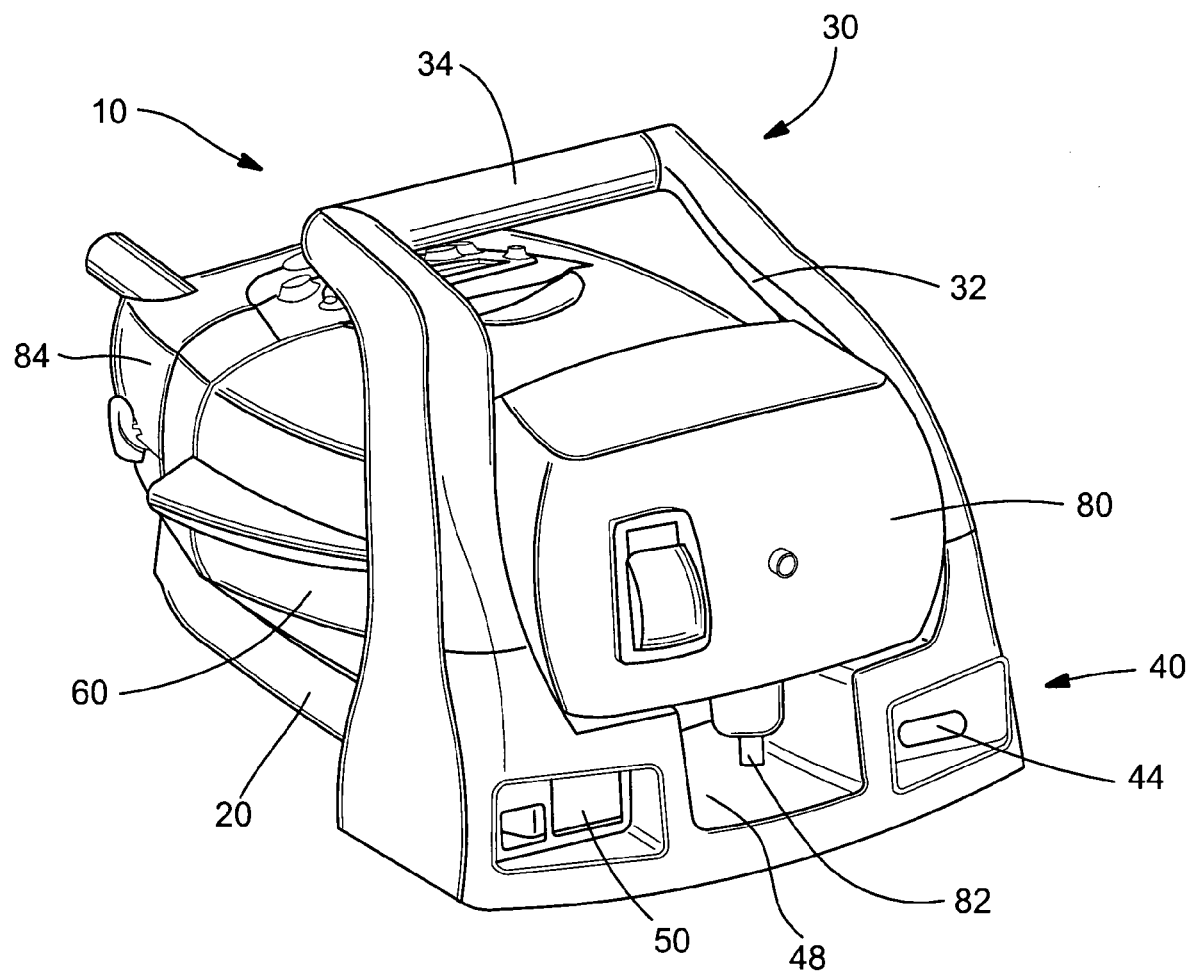
FIG. 10 is a rear perspective view of the portable cradle, PAP device, oxygen blender, and humidifier of FIG. 6.

FIGS. 6-10 show that the top 42 of the body portion 40 is designed to receive accessories to the PAP device 60, such as an oxygen blender 80. The top 42 of the body portion 40 is located away from the base 20 a suitable distance such that the oxygen blender 80 may rest on top 42 of the body portion 40 and be correctly aligned with the PAP device 60 such that the proper connections can be made between the oxygen blender 80 and the PAP device 60. The oxygen blender 80 may connect to the PAP device 60 both physically and pneumatically. Further, the oxygen blender 80 may be electrically connected to the base 20. FIG. 10 shows an oxygen filter 82 attached to the oxygen blender 80 and protected by a recessed portion 48 of the body 40.

Figure 11:
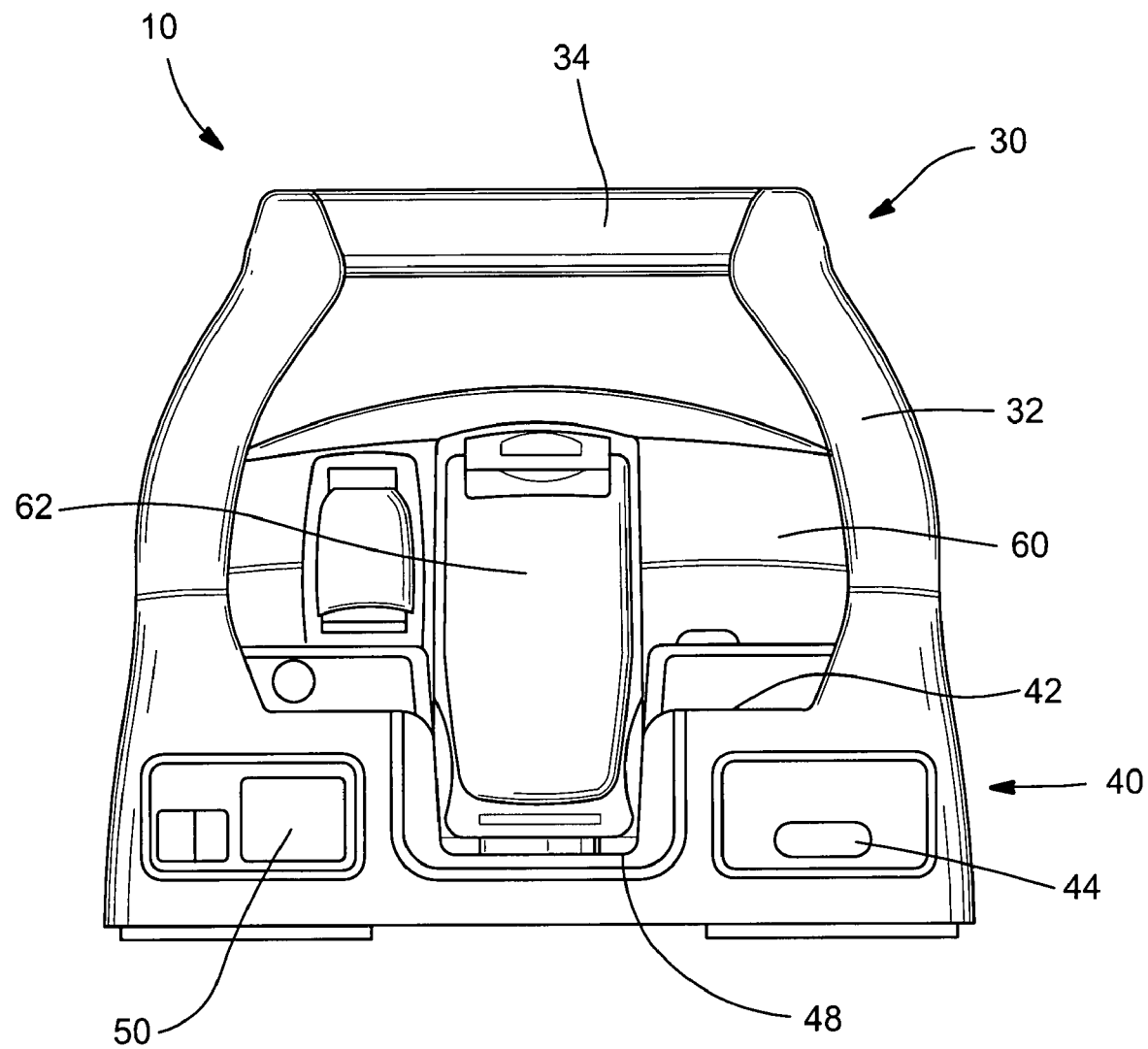
FIG. 11 is a rear view of the portable cradle and PAP device of FIG. 4 with a data module attached to the PAP device.

FIG. 11 shows that the recessed portion 48 of the body 40 allows a data or patient management module 62 to be attached to the PAP device 60 such that data can be downloaded from the PAP device 60 and transferred to a computer or some other external device. U.S. Design Pat. No. D486,916 shows further features of the data module 62 and is incorporated herein by reference in its entirety.

1.7 Openings for Passing Cords and/or Cord Storage

As shown in FIG. 1, the body portion 40 may further include at least one opening. In the illustrated embodiment, the body portion 40 includes openings 44 and 46. As illustrated, the opening 44 may be utilized to run communication cords 65 from one component to another, and the opening 46 may be utilized to run communication cords 64, such as power cords, data communication cords, or plugs, from one component to another. For example, a power cord from the PAP device 60 may be passed through the opening 46 in the cradle 10 to the oxygen blender 80 or the battery module 70.

Also shown in FIG. 1, the openings 44 and 46 may also define or compose storage compartments to store and conceal the actual communication cords. In an embodiment, the communication cords are stored on the cradle 10 such that only the main components of the breathing apparatus need to be moved to the cradle 10 to make the breathing apparatus portable. For example, a data communications cord can be stored in a storage compartment 44 towards one end of the body portion 40 while a power cord can be stored in a storage compartment 46 towards the opposite end of the body portion 40. The positioning of the storage compartment 46 may correspond with the location of the attachment port on the PAP device 60.

Any communication cords that may be stored within the storage compartments 44 and 46 of the body portion 40 are pulled out far enough to connect them to the appropriate connection point located on the PAP device 60.

1.8 Master Power Switch

As shown in FIGS. 4 and 11, the body portion 40 may further include a master power switch 50. The master power switch 50 allows the user to press one button to turn the PAP device 60 and oxygen blender 80 on and off. The master power switch 50 is internally wired. That is, any power cord that is needed to connect the PAP device 60 to the master power switch 50 cannot be seen from the outside of the cradle 10.

1.9 Exemplary Usage

To use the cradle 10 of the illustrated embodiment, the cradle 10 is connected to the battery module 70 by indexing the at least one engageable member of the second side 24 of the base 20 of the cradle 10 with the complementary at least one engageable member of the battery module 70 and securing the cradle 10 in place. The battery module 70 can then be placed on a supporting surface, which orients the first side 22 of the base 20 of the cradle 10 to an upward facing position.

After the cords are attached to the PAP device 60, any excess cordage is fed back into its storage compartments 44 and 46 as the at least one engageable member disposed on the PAP device 60 is indexed with the at least one engageable member 26 of the first side 22 of the base 20 of the cradle 10. At this point, compartment 46 may not be used for cord storage as it may have plugs that make automatic power connections and ensure that the power switch is on. When the PAP device 60 is properly aligned with the cradle 10, the PAP device 60 is secured onto the cradle 10 by moving the PAP device 60 in the appropriate direction. When the PAP device is positioned, secured, and/or locked onto the cradle, compartment 44 may be used for communication cord storage. Additional accessories to the PAP device 60, such as oxygen blender 80, can now be attached to the PAP device 60 and secured onto the cradle 10 by attaching any appropriate communication cord/plug to the accessory and resting the accessory on the cradle 10 and moving the accessory into a fully secured position.

When all of the components of the breathing apparatus are fully attached and secured to the cradle 10, the master power switch 50 can be used to turn on the breathing apparatus. The user can now lift the cradle 10 by the handle 30 and easily walk around with the now truly portable system.

It is understood that any references to direction, such as horizontal, upward or downward, should not be considered to be limiting and are used solely as a point of reference to better exemplify the embodiments discussed herein.

Also, in alternative embodiments, the cradle 10 may include flying-lead wire connections, fixed electrical connectors (both data and power), and wireless-type data transfer means (e.g., infrared, bluetooth, etc.) to transfer signals between modules.

2. Device to Deliver a Range of Different Modes

Figure 12:
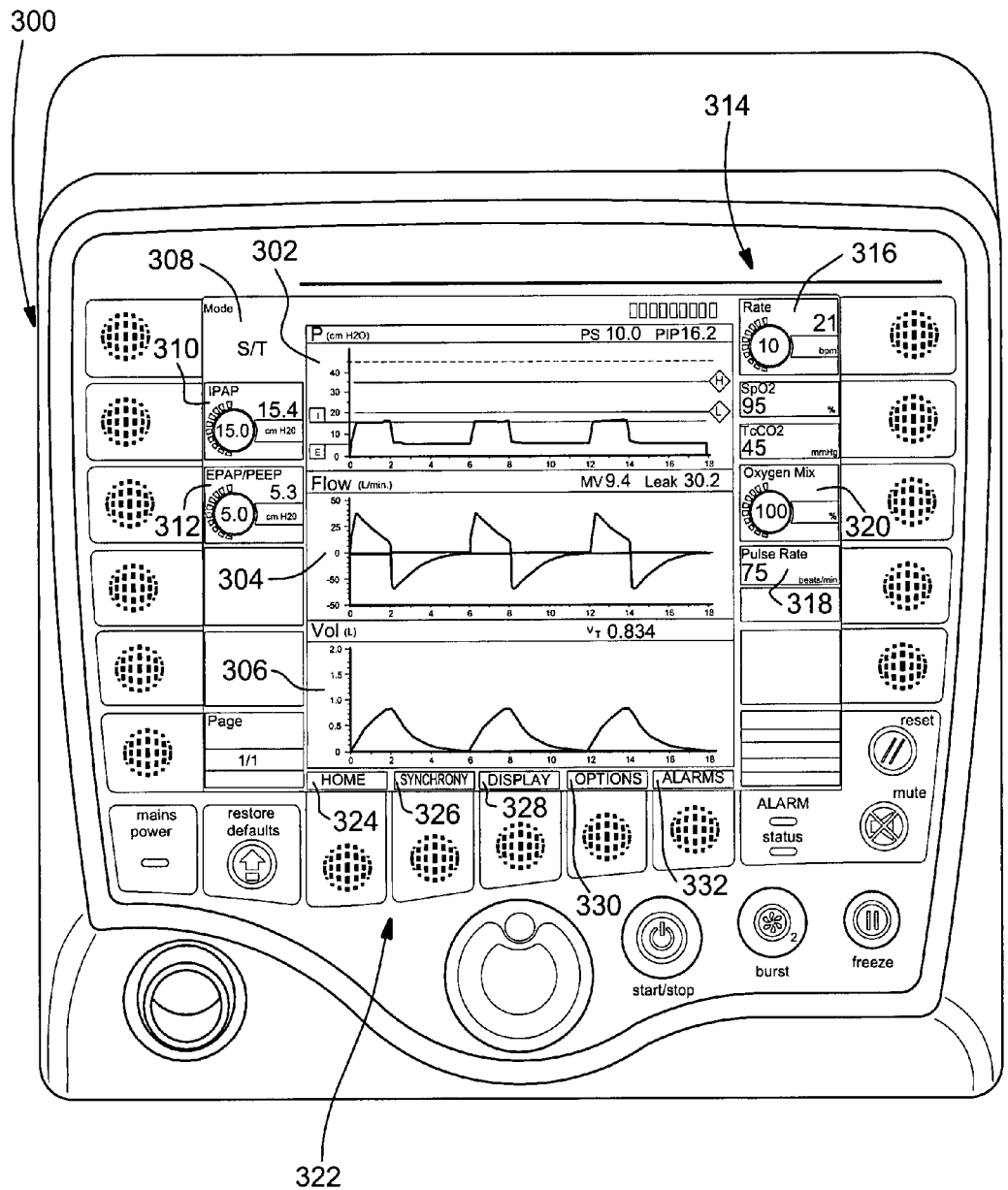
FIG. 12 is a front view of a display screen for a PAP device system according to an embodiment of the present invention.

A PAP device in accordance with an embodiment of the invention includes a blower, controller, and programmable display screen. An exemplary embodiment of the programmable display screen 300 is shown in FIG. 12. In an embodiment, the device would be capable of supplying air at positive pressure in the range of at least 4 to 20 cm $H_2O$, and would provide easy selection of a range of nasal CPAP modes including CPAP, APAP, VPAP and CS-2 waveforms.

The device may be used with a patient interface system including an air delivery conduit and mask system such as a nasal mask, full-face mask, or nasal prongs. Also, the device may be coupled with a humidifier to provide humidified air to a patient. In an embodiment, the humidifier is placed between the PAP device outlet and the air delivery conduit.

The programmable display screen 300 of the device allows the clinician to easily program the device to deliver the desired treatment mode. Another advantage is that if the patient is not comfortable with the initial treatment mode, the clinician can easily adjust the treatment mode to expose the patient to alternative treatment delivery modes. This saves time, storage space, and effort for the clinician and allows more efficient selection of the appropriate device for the patient.

As illustrated in FIG. 12, the programmable display screen 300 clearly illustrates and allows control of various parameters of treatment. For example, the display screen 300 illustrates graphs of the pressure 302, flow 304 and volume 306 of applied air. In addition, the display screen 300 specifies the mode 308, the pressure at inspiration 310 and expiration 312, and various heart monitoring parameters 314, e.g., heart rate 316, pulse rate 318, oxygen mix 320. Further, the display screen 300 includes various programming menus 322, e.g., home 324, synchrony 326, display 328, options 330, and alarms 332.

It should be understood that the programmable display screen 300 and associated controller may be incorporated into the PAP devices described above, e.g., to provide alternative treatment modes.

3. Device Configurable to a Patient's or Clinician's Requirements

Another aspect of the invention relates to a breathing system that is configurable in accordance with requirements of the patient and the clinical pathway in which it is utilized. Specifically, the breathing system may be configured in an efficient manner so as to allow for the provision of therapy consistent with patient requirements and the chosen clinical pathway. In an embodiment, the breathing system may be configurable along the clinical pathway both upwardly and downwardly. That is, the breathing system may be configurable for patients requiring different intensities of care, e.g., patients that require a high level of care by the clinician, patients that require a low level of care by the clinician, and anywhere in-between.

An aspect of the invention allows for the requisite degree of device support to be maintained while the complexity and multiplicity of functionality is reduced or increased to a level that is consistent with the patient's needs. For example, a patient may be identified as a candidate that is to be managed in accordance with a high level in the clinical pathway. This position may dictate intensive care involving the monitoring of multiple physiological parameters and the trying of various ventilatory assist regimes. The aim is to determine the patient's condition, monitor fluctuations in that condition, and attempt to stabilize an acute situation. The delivery of treatment gas, such as oxygen-enriched air, may also be required.

This initial stage may occur with the patient being admitted to a clinic intensive care unit. While in the intensive care unit, the fully configured breathing unit may be utilized to its full advantage. The fully configured breathing unit may include physiological sensors for performing direct monitoring of breathing parameters such as flow and pressure (e.g., by a patient interface such as a cannulae, facials mask, or full-face mask). In addition, the patient interface may be used to deliver medicinal gas such as oxygen enriched air, bronchodilator, and cardiovascular treatment pharmaceuticals. Also, other physiological parameter sensors (such as pulse oximetry, $CO_2$ level sensor, blood pressure, temperature, and ECG transducers) may be applied to the patient. In an embodiment, the fully configured breathing unit will allow for the receiving of the output of the transducers and thereby serve to centralize the collection, analysis, storage, and transfer of data. The relevant data can be observed on the displays of the PAP device, the cradle or at a remote location. For example, the display screen may be configured such as that shown in FIG. 12 which shows various parameters of treatment.

By decision of the supervising clinician or through use of a self-adjusting algorithm, the NIPPV treatment delivered to the patient may vary over time. For example, in U.S. Pat. No. 6,336,454, it is taught that a stroke patient should received CPAP during the first three hours following a stroke event. An aspect of the invention may be directed to providing this treatment to the patient. As the patient processes and stabilizes or other requirements are recognized, the treatment may be varied so as to address the patient's particular needs. The fully configured breathing system capable of performing these tasks may be considered to be complex in functionality and appropriately utilized in a supervised clinical environment such an intensive care unit. Once the patient has stabilized, then the need for intensive monitoring and care may be reduced. At this point, the breathing system may be reconfigured so as to just maintain the requisite level of functionality.

The reduced functionality device configuration may continue to service the patient. Since the elements making up the reduced functionality device configuration were present in the fully configured breathing unit, the patient's exposure to change and associated stress is not dramatic. This also has the advantage of facilitating the patient becoming involved in their treatment as soon as their condition allows. For example, even when they are in the intensive care unit, the patient may be introduced to the breathing system and provided with instruction on the operation of the reduced functionality device configuration to which hopefully they will progress. The assigned reduced functionality device configuration may remain serving the patient and may literally travel with patient through the clinical pathway out of the intensive care until, to a clinical observation unit, and finally to the patient's domestic environment. By the provision of an appropriate power source, such as a battery array, the patient need not be detached from the device at any time and treatment is maintained. The device may be easily reconfigured to the requisite level of functionality at home, the observation ward or intensive care unit, and while in transit between such locations. Similarly, by incorporating the appropriate data recording or transfer modules as envisaged by aspects of the invention, it is possible to maintain a record of the physiological parameters and device performance as may be considered relevant to the clinical pathway.

Of course, if the patient is not maintained on the device that was first utilized in the intensive care unit, a similar if not identical device may be readily substituted with minimum interference to the patient. Because of this modularity, the parameters of device operation peculiar to a patient (e.g., gathered or determined by the fully configured breathing system) may be readily transferred to the substitute unit via any appropriate data exchange system such as device-to-device wireless or wired link, a local or web based network, or physical data transfer media systems such as by SmartCard.

The continuity of association between a patient and treatment devices afforded by an embodiment of the present invention allows for a gaining of familiarity and minimal need for the patient to retain or readjust to medical devices required to properly monitor the patient's condition whatever their progress along the applicable clinical pathway. Such minimization of change facilitates the patient's involvement in and compliance with treatment and eventual success. It also allows for a flexible approach to managing responsibility for resource demarcation and allocation. The various modules making up the breathing systems of the present invention, the clinical decisions determine their use, and the consequent costs of acquisition, utilization and maintenance are easily identified and allocated by reference to each physical module.

For example, experience may teach that at any one time an intensive care unit has no more than three patients receiving oxygen while on NIPPV. At the same time, there may be seven patients on NIPPV. Similarly, data transfer may only be required to occur from two units at any one time while the clinical pathway mandates that each patient remain on NIPPV as they are transferred to another ward. In this example, the intensive care unit would only need three oxygen modules, two data transfer modules, and seven cradles equipped with batteries. The clinic's inventory system would also determine whether it transferred patients onto exchange PAP devices when they leave the intensive care unit. In any event, the clinic would have in stock many PAP devices in order that each patient may take home the same PAP device that was assigned to them while at the clinic. The clinic can then transfer the cost of the PAP device to the appropriate funding source, which source may be different to the funding source responsible for the cost of acquiring and maintaining the oxygen module, cradle, and other high functionality units used in the intensive care unit. This is only one example of how aspects of the present invention allow for the efficient and clinical optimum management of NIPPV devices.

Thus, an aspect of the invention relates to a mechanical ventilator assembly or breathing unit that is adapted for use in the ICU and home (and everywhere in-between). The mechanical ventilator assembly may include structure having a blower (PAP device), an interface including buttons and displays, a housing which may be removably mountable on a stand, and a cradle adapted to receive the PAP device.

In an embodiment, the mechanical ventilator assembly may be assigned to continue on all patients that leave the intensive care unit. Educating the patient and empowering them to be actively involved in their treatment can have a significant impact on compliance to treatment and achieving compliance is the critical first step to ensuring effective treatment. An aspect of the invention is to increase the level of intervention, and once withdrawn, the functionality may be redeployed to other units being used on other patients.

4. Trolley

Figure 13:
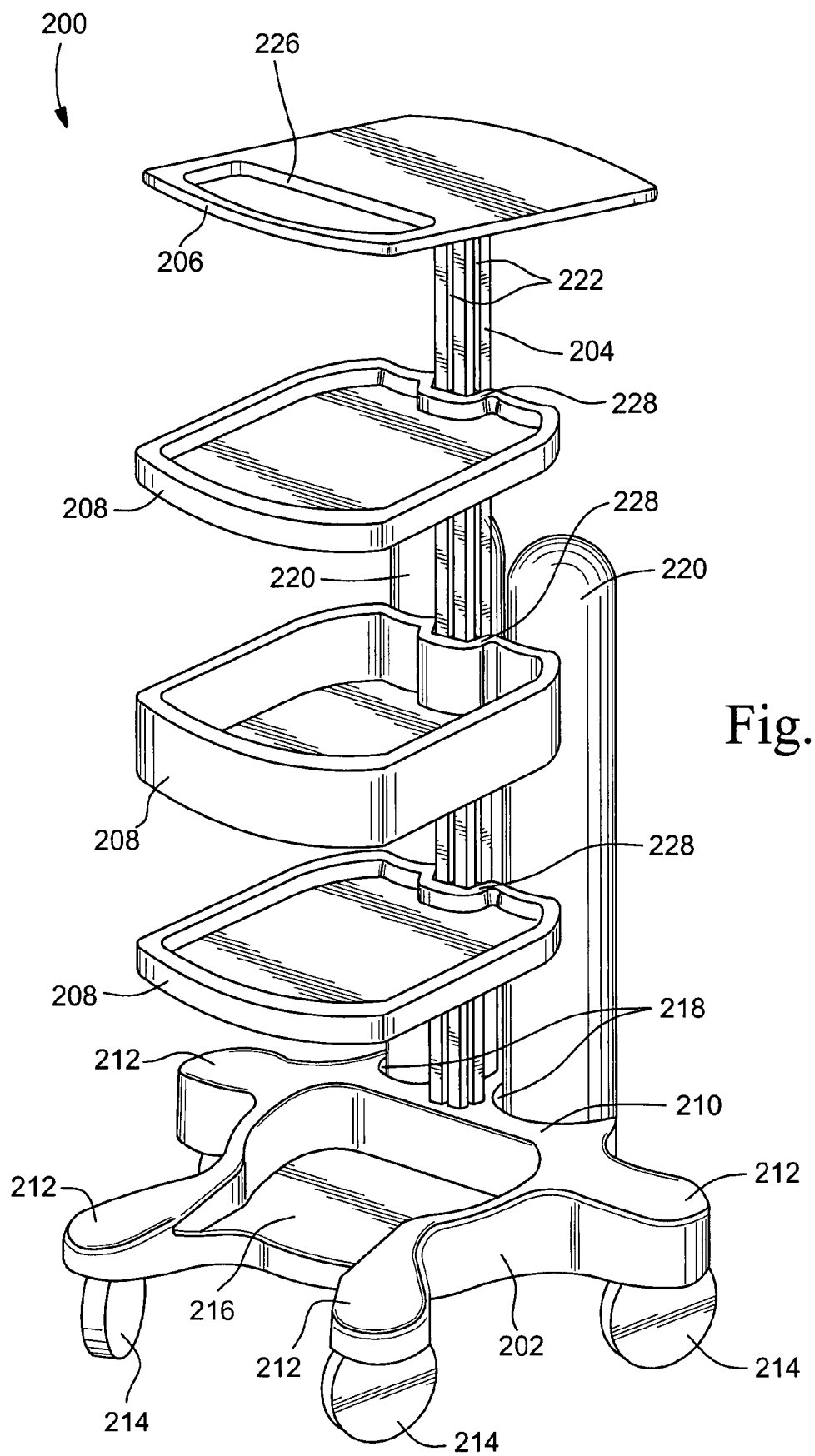
FIG. 13 is a perspective view of a trolley according to an embodiment of the present invention.
Figure 14:
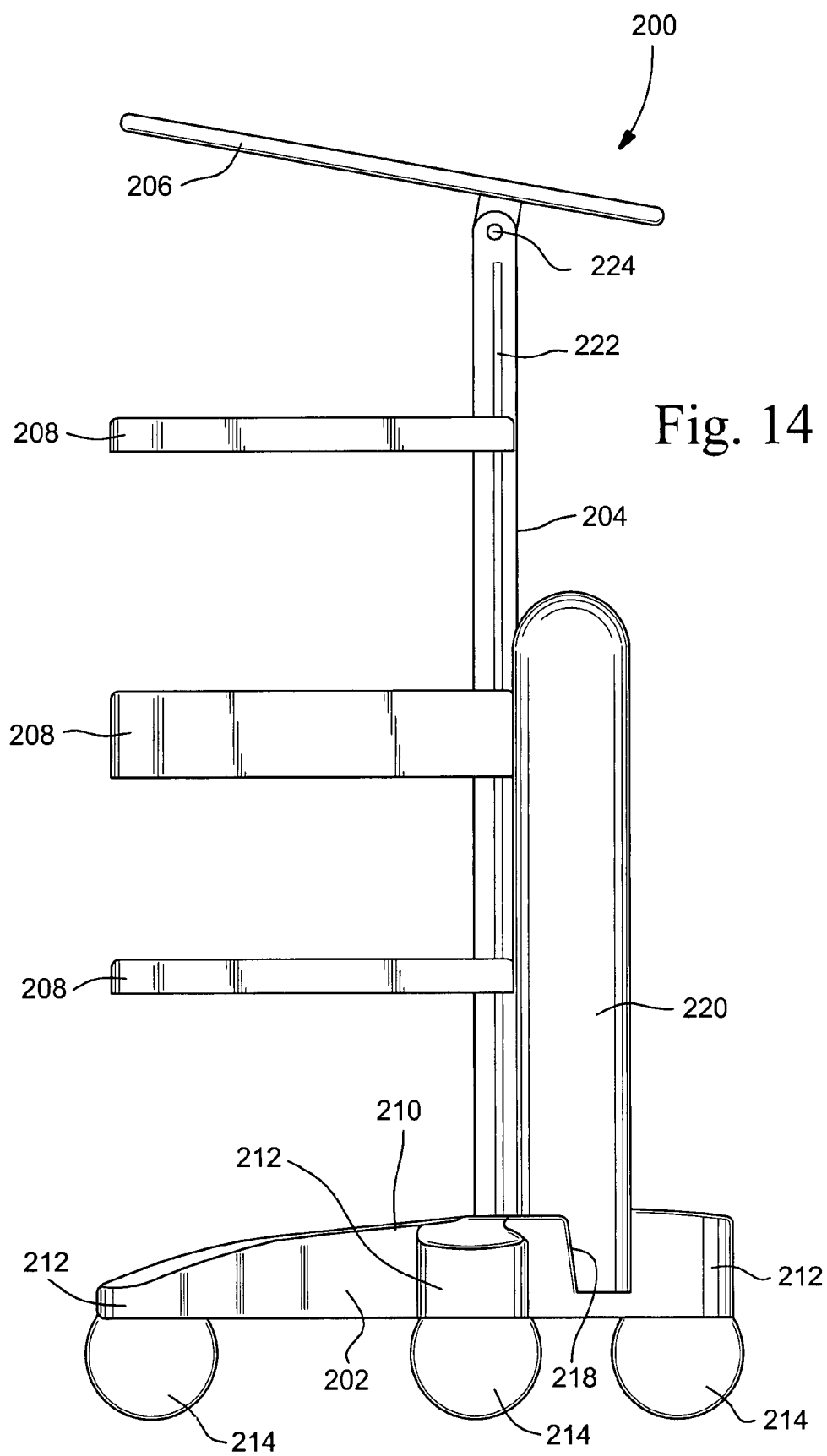
FIG. 14 is side view of the trolley shown in FIG. 13.
Figure 15:
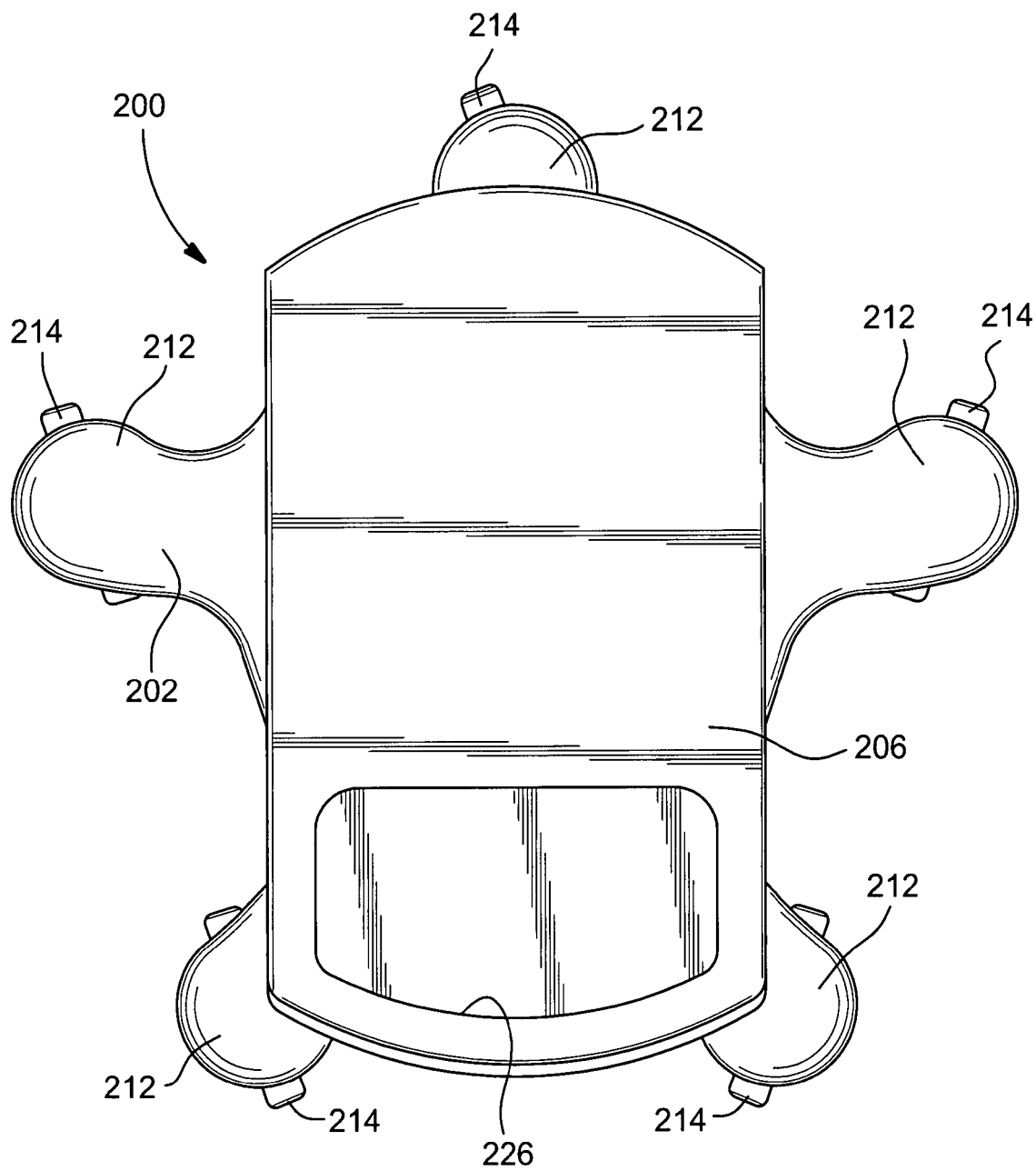
FIG. 15 is top view of the trolley shown in FIG. 13.

FIGS. 13-15 illustrate a movable support stand or trolley 200 that may be used with breathing apparatuses such as those described above. As illustrated, the trolley 200 includes a wheel base 202, a support pole 204 provided to the base 202, a handle 206 provided to a free end of the support pole 204, and one or more storage shelves or bins 208 provided along the support pole 204.

As illustrated, the wheel base 202 includes a base portion 210, five prongs 212 extending from the base portion 210, and five wheels 214 supported by respective prongs 212. The five pronged wheel base 202 provides stability to prevent tipping of the trolley 200 in use. However, other wheel arrangements are possible. Also, the base portion 210 has a narrow width to allow the trolley 200 to fit between hospital beds in use for example.

In the illustrated embodiment, the base portion 210 includes a recessed storage area 216 for storage purposes. For example, the storage area 216 may be used to store a battery, e.g., external battery, for supplying power to a breathing apparatus supported on the trolley 200. The base portion 210 also includes a pair of recessed areas 218 for oxygen storage. For example, the recessed areas 218 may store oxygen cylinders 220 each having an Australian "C" size or U.S. "E" size. However, the recessed areas 218 may have other suitable sizes for storing other size oxygen cylinders.

Also, one or more of the wheels 214, e.g., front two wheels, may include brakes to prevent movement of the trolley 200. In an embodiment, each wheel 214 has a diameter of about 125 mm. However, other wheel sizes are possible.

The support pole 204 is mounted to the wheel base 202 and extends vertically therefrom. As best shown in FIG. 14, the support pole 204 is offset to a rear of the wheel base 202 so that the shelves or bins 208 do not extend beyond the footprint of the wheel base 202 in use. Also, the support pole 204 includes a slotted configuration 222 for attaching the storage shelves or bins 208 in user preferred configurations.

The handle 206 is pivotally attached to the free end of the support pole 204 opposite the wheel base 202. The pivotal attachment allows pivotal movement about an axis 224 so that the angle of the handle 206 may be easily adjusted to suit different user heights. In the illustrated embodiment, the handle 206 has a smooth plate-like configuration with an elongated hand opening 226. This structure allows the handle 206 to protect the equipment supported on the shelves or bins 208 below it. In an embodiment, the handle 206 is positioned 910-1000 mm from the ground, and the hand opening 206 has a 25-40 mm diameter and a 50 mm minimum knuckle clearance. However, other suitable dimensions are possible.

The one or more storage shelves or bins 208 are removably attached to the support pole 204. In the illustrated embodiment, the trolley 200 includes two relative shallow storage shelves and a relatively deep storage bin between the shelves. However, other shelf arrangements are possible.

The shelves and bin 208 provide an arrangement that is open and easy to clean. In an embodiment, the shelves and bin 208 each provide a storage area of about 250×250 mm. However, other suitable sizes are possible.

Also, each of the shelves and bin 208 include a recessed attachment portion 228 (e.g., see FIG. 13) that is removably attachable to the support pole 204. Specifically, the recessed attachment portion 228 is structured to releasably interlock with the slotted configuration 222 of the support pole 204. This arrangement allows the user to position the shelves or bins 208 at desired positions depending on application. Further, the shelves or bins 208 are easily removable for rearrangement and/or cleaning purposes.

In use, the trolley 200 may be easily wheeled to its desired location and the removable shelf arrangement allows storage of multiple accessories. For example, a shelf 208 may support a PAP device such as PAP device 60 described above. In an embodiment, a shelf 208 may be configured to take the form of base 20 described above. Other accessories supported by the trolley 200 may include an IV and IV hook-ups.

5. Additional Battery Pack Embodiments

Figure 16:
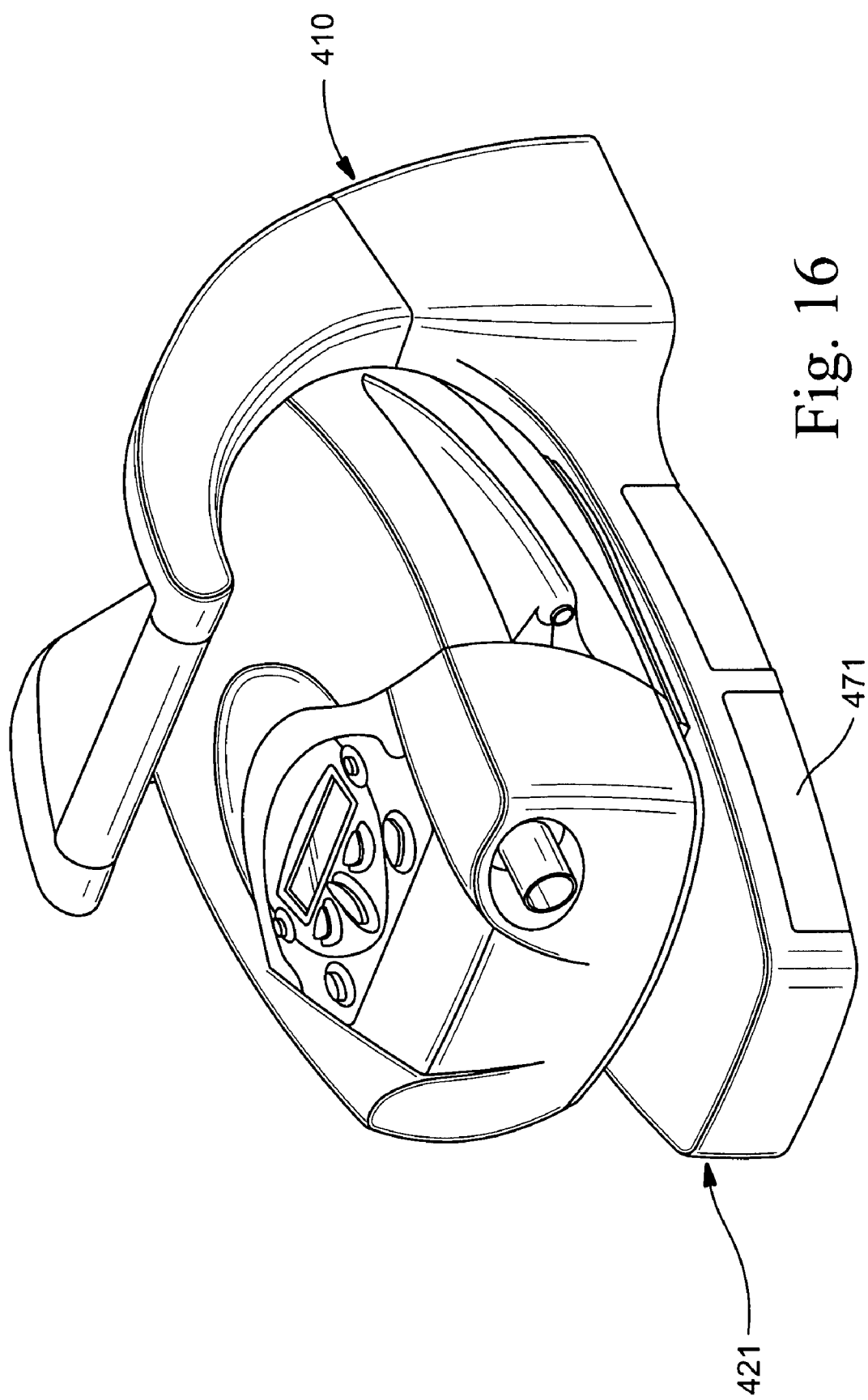
FIG. 16 is a perspective view of a battery pack embodiment of a cradle provided with detachable, rechargeable batteries.

FIG. 16 illustrates an embodiment of the cradle 410 provided with at least one detachable, rechargeable battery 471. In this embodiment, two detachable, rechargeable batteries 471 are provided. In this configuration, with at least two batteries 471, the cradle becomes hot swappable, that is, one battery 471 can be exchanged while another battery 471 powers the unit. This allows a cradle user, medical personnel, etc. to charge an extra battery while the cradle is in use, and then swap the battery in while providing perpetual power to the cradle. According to the illustrated embodiment, the cradle base 421 has been adapted to provide space for battery 471 insertion. Although the illustration shows two batteries 471, any number of batteries may be used.

Figure 17:
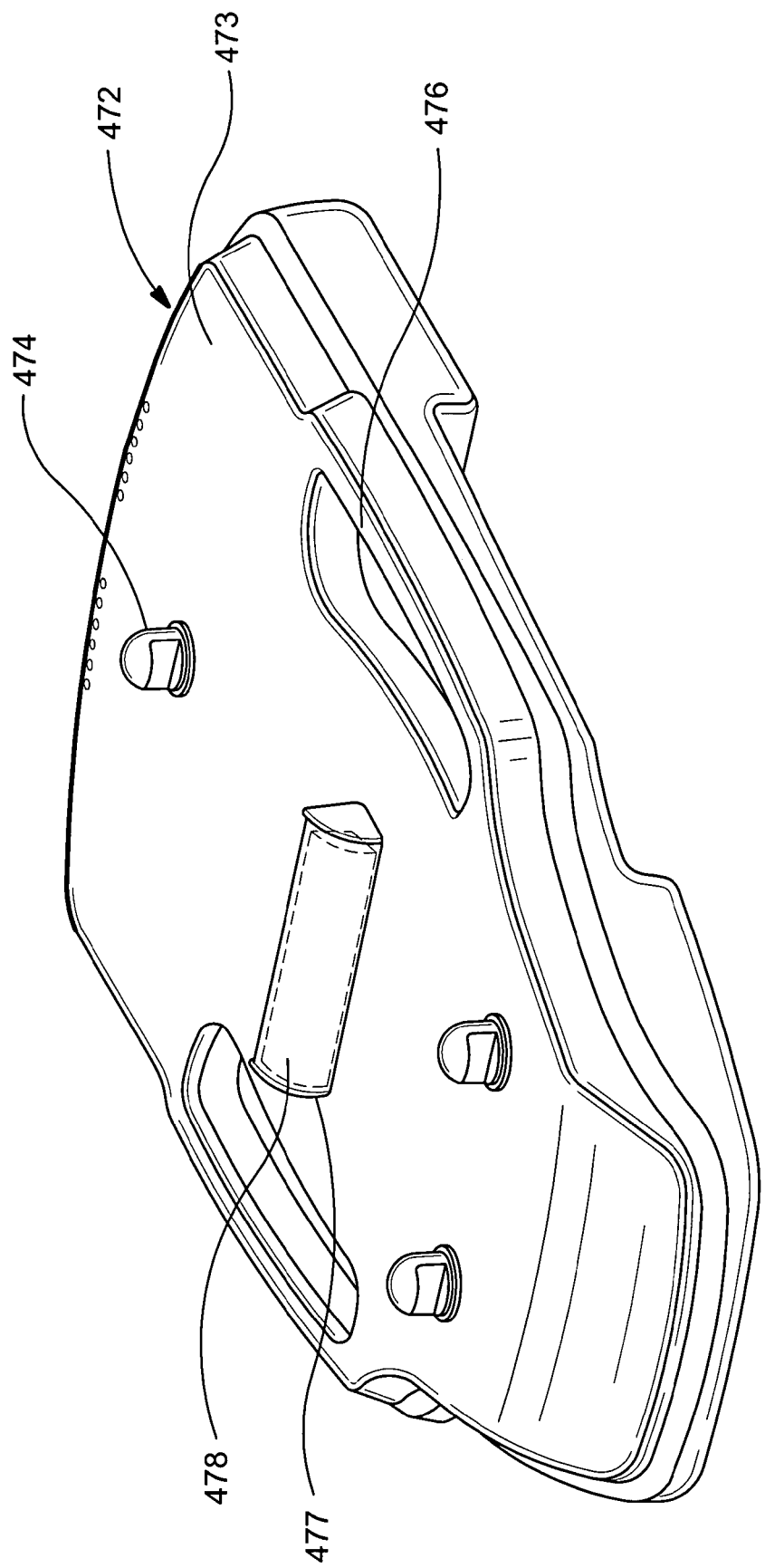
FIG. 17 is a perspective view of a battery pack that may be used with a cradle.

FIG. 17 illustrates a battery pack 472 that may be used with the cradle. The battery pack 472 as illustrated is fully detachable and may be provided with at least one battery handle 476. In this embodiment, there are two battery handles 476 provided along the sides of the battery pack 472, allowing the battery pack 472 to be gripped and carried from either side. The illustrated battery pack 472 also is provided with at least one engagement pin 474. The engagement pins 474 are positioned on a first surface 473 of the battery pack 472 and are arranged so as to coincide with at least one receiving hole which would be provided in a cradle to which the battery pack 472 is to be attached. It is contemplated that a sufficient number of receiving holes will be provided to receive the engagement pins 474. Additional receiving holes can also be provided to fit a variety of engagement pin configurations. In the illustrated embodiments, the pins 474 are further configured to engage a cradle locking plate (421 in FIG. 18), which locks the battery pack 472 to the bottom of the cradle. In this illustrated embodiment, the battery pack 472 also includes a power and communication center 478 with a flip down lid 477. Although the embodiment as illustrated shows three engaging pins 474 and two handles 476, any number or configuration of engaging pins and handles may be used. Further, the lid may be spring loaded to slide back into a covering position when the battery pack is disengaged from the cradle.

Figure 18:
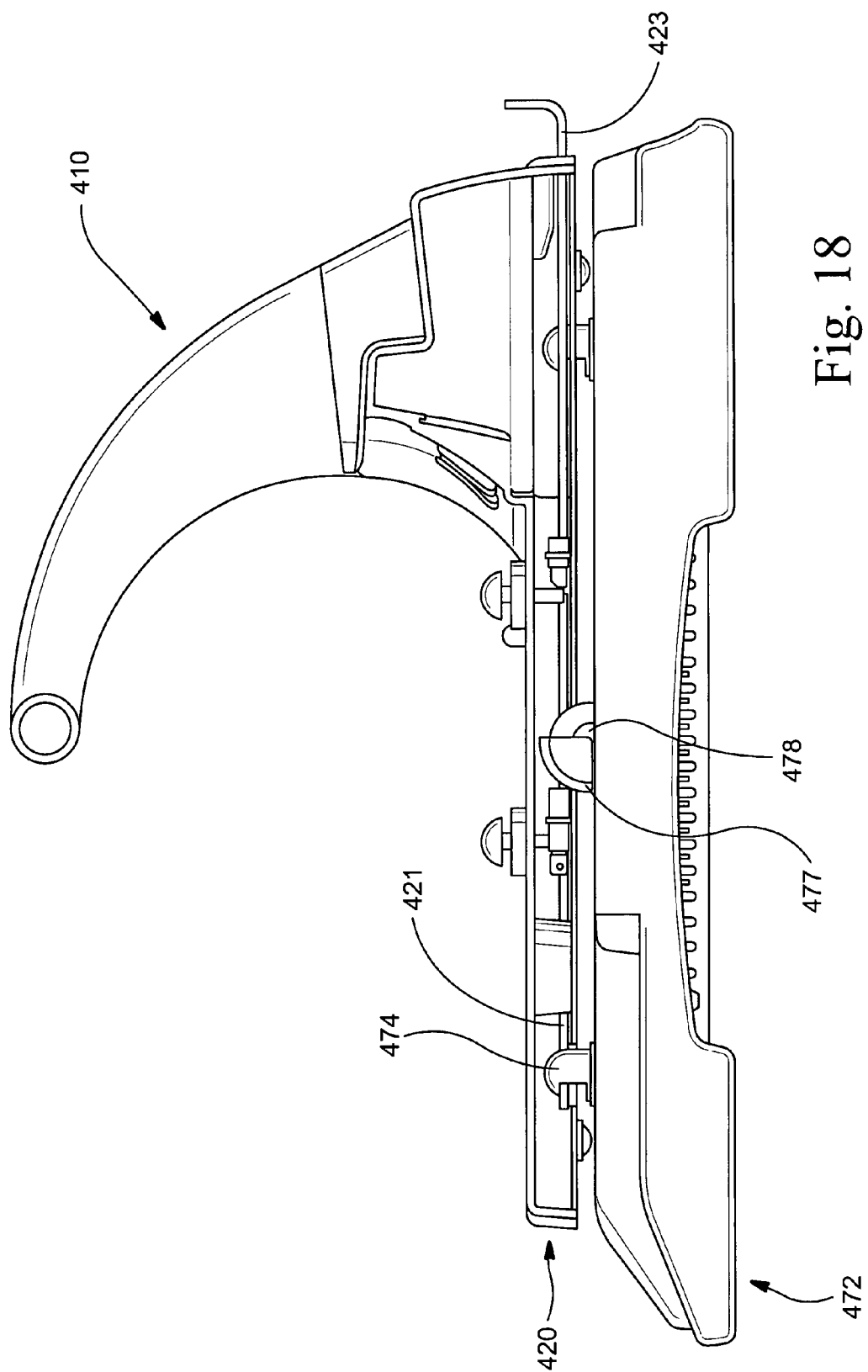
FIG. 18 is a side view of the battery pack of FIG. 17 engaged with a cradle shown in cross-section.

FIG. 18 shows a side view of the battery pack 472 of FIG. 17 engaged with a cross-section of a cradle 410. Each of the engaging pins 474 has been locked into the base 420 of the cradle 410 and is held in place by locking plate 421. The flip down lid 477 has been pushed back, exposing the power and communications connector 478. The flip down lid 477 may be further spring loaded such that it springs back into position when the battery pack 472 is disengaged from the cradle 410. The locking plate aids in holding the battery module to the cradle, helping to prevent the battery from accidental disengagement.

If a user desires to disengage the engaging pins 474 from the locking plate 421 and remove the battery pack 472, the user pulls on the locking plate release handle 423. It is contemplated that other suitable method for disengaging the locks may be used. In one exemplary embodiment, a locking method that is simple enough for a home user to easily change the battery pack is employed.

Figure 19:
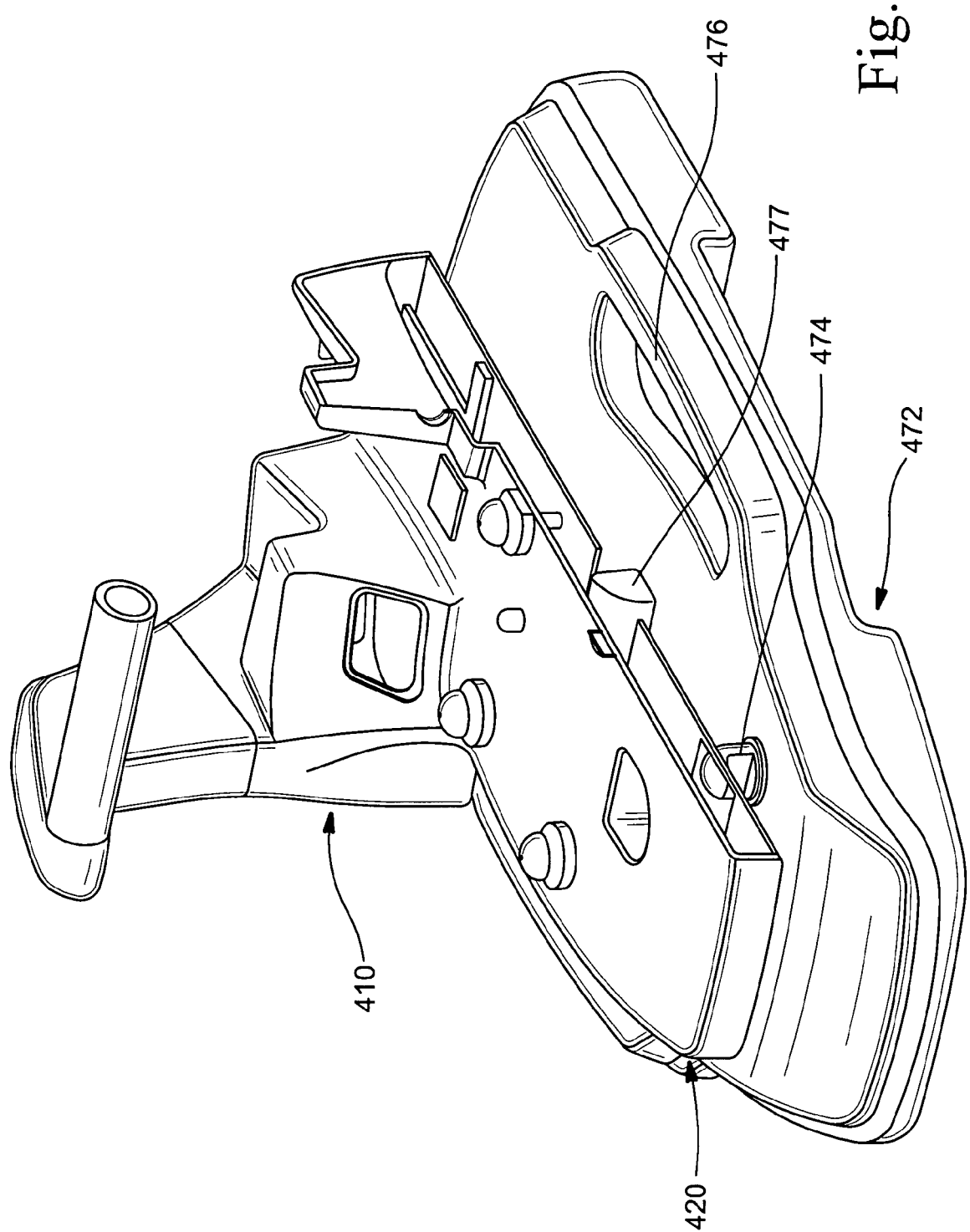
FIG. 19. is a perspective view of the battery pack/cradle combination of FIG. 18.

FIG. 19 shows a perspective view of the battery pack 472 and cradle 410 combination of FIG. 18. Again, the engaging pins 474 have engaged the cradle 420, and the cradle has pushed back the flip-down lid 477. From this view, a battery pack handle 476 is also visible. With the pins engaging the cradle, the cradle can also be carried by the battery pack handle with less concern about the cradle accidentally disconnecting from the battery and falling to the ground.

Figure 20:
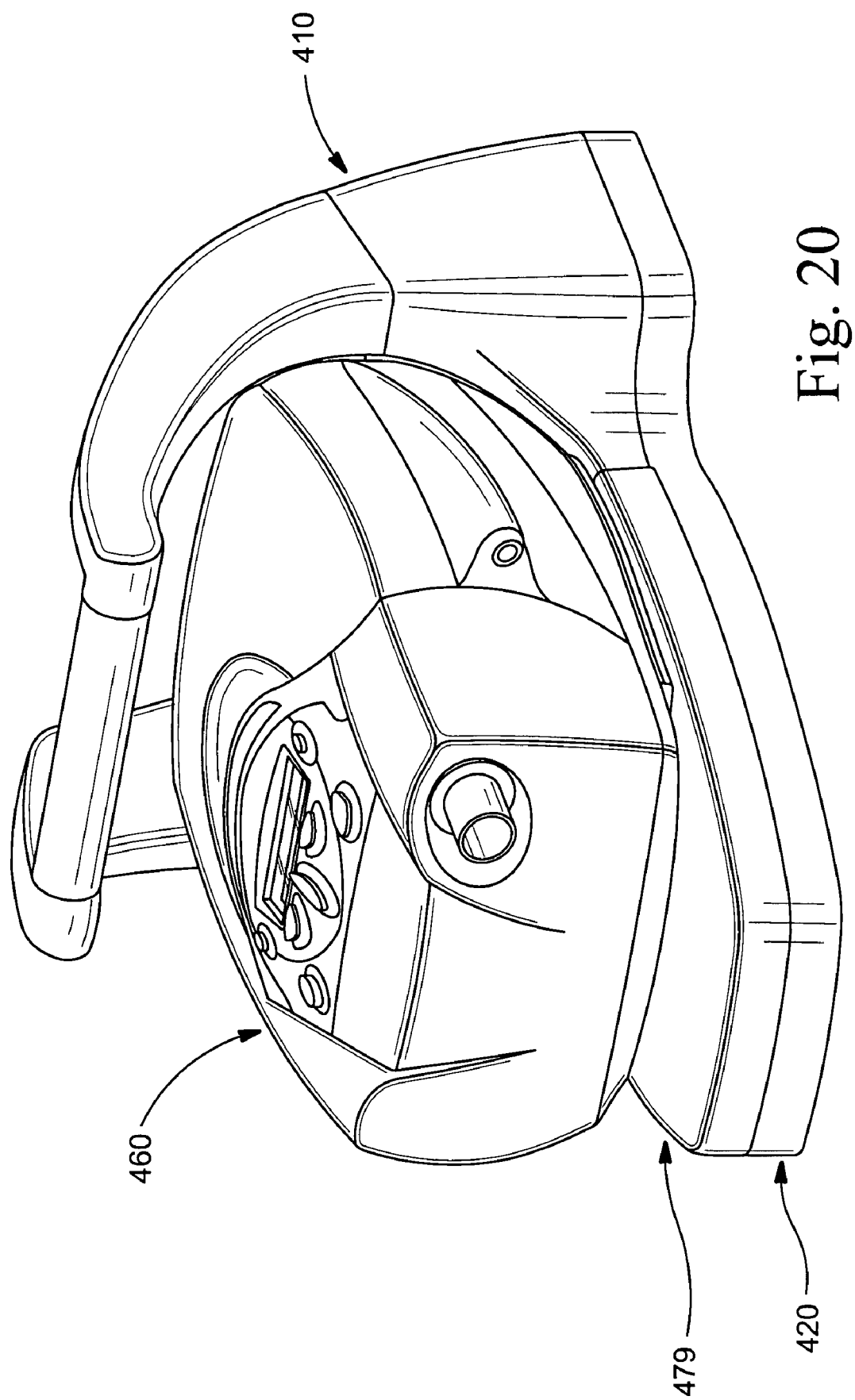
FIG. 20 is a perspective view of a configuration of a battery pack and cradle combination according to an embodiment of the present invention.

FIG. 20 shows a perspective view of a configuration of a battery pack 479 and cradle 410 combination. According to the illustrated embodiment, the battery pack 479 in this configuration is interposed between the PAP device 460 and the cradle base 420. In this embodiment, the battery pack is shaped to match the contours of the cradle, and incidental parts of the battery pack that might accidentally snag on something do not protrude.

It is contemplated that battery packs of any configuration, shape, and size may be used, with the variances between these factors depending on where the battery will be used, whether handles are desired, etc.

6. Additional Cradle Embodiments

Figure 21:
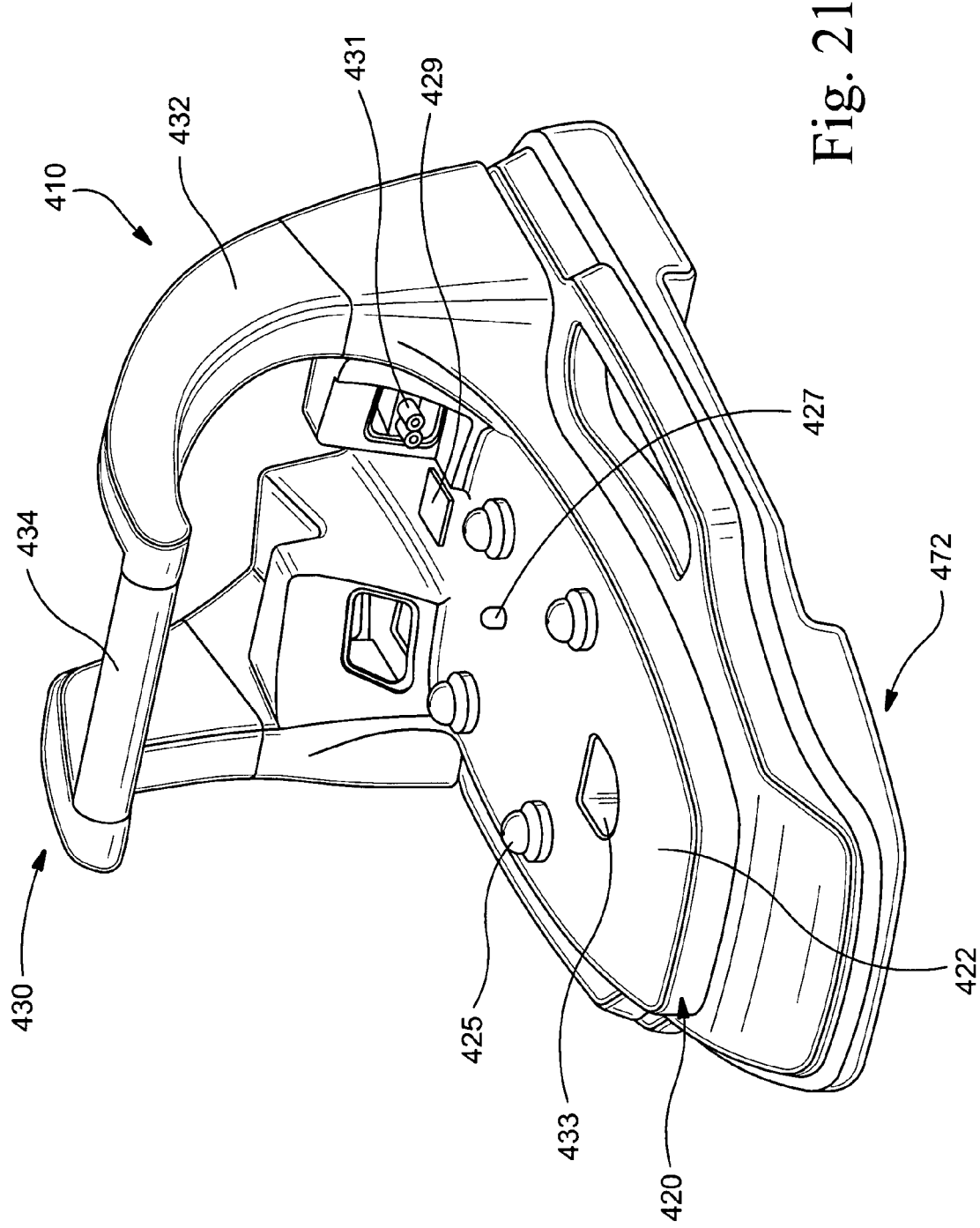
FIG. 21 is a perspective view of a cradle provided with a plurality of engaging pins disposed on a first side of the cradle base according to an embodiment of the present invention.

FIG. 21 shows a perspective view of a cradle 410 provided with a plurality of engaging pins 425 disposed on the first side 422 of the cradle base 420. These pins 425 are configured to engage engagement tabs provided on the bottom of a PAP device e.g. see engagement tabs 461 in FIG. 23. According to this illustrated embodiment, an additional locking pin 427 may also be provided. The locking pin protrudes through the first side 422 of the cradle base 420, and is designed to engage a receiving portion provided on the bottom of a PAP device e.g. see receiving portion 463 in FIG. 23. The locking pin may be released or otherwise disengaged from the receiving portion by a lock release button 429. Other suitable methods of securing the PAP device to the cradle, such as latches, releasable tabs, etc. may also be used.

In addition to the engaging pins 425, the cradle 420 in the illustrated embodiment has been provided with a handle 430 having at least one arm 432 and at least one carrying portion 434. Preferably, the at least one handle arm 432 will provide sufficient clearance to allow a user to grip the handle 430 while a PAP device is attached to the cradle 420. Using the handle 432, the PAP device can be carried from place to place, and when a battery is attached to the cradle the PAP device can be portably powered as well. The base has also been provided with an access hole 433 allowing a humidifier attachment to be released from a PAP device without having to disengage the PAP device from the cradle. The cradle also has electrical connections 431 which may be attached to the PAP device. This allows the PAP device to continue to operate while attached to the cradle while the humidifier is refilled, cleaned, replaced with another device, etc. In this illustrated embodiment, a battery pack 472 is also attached to the cradle 410.

Figure 22:
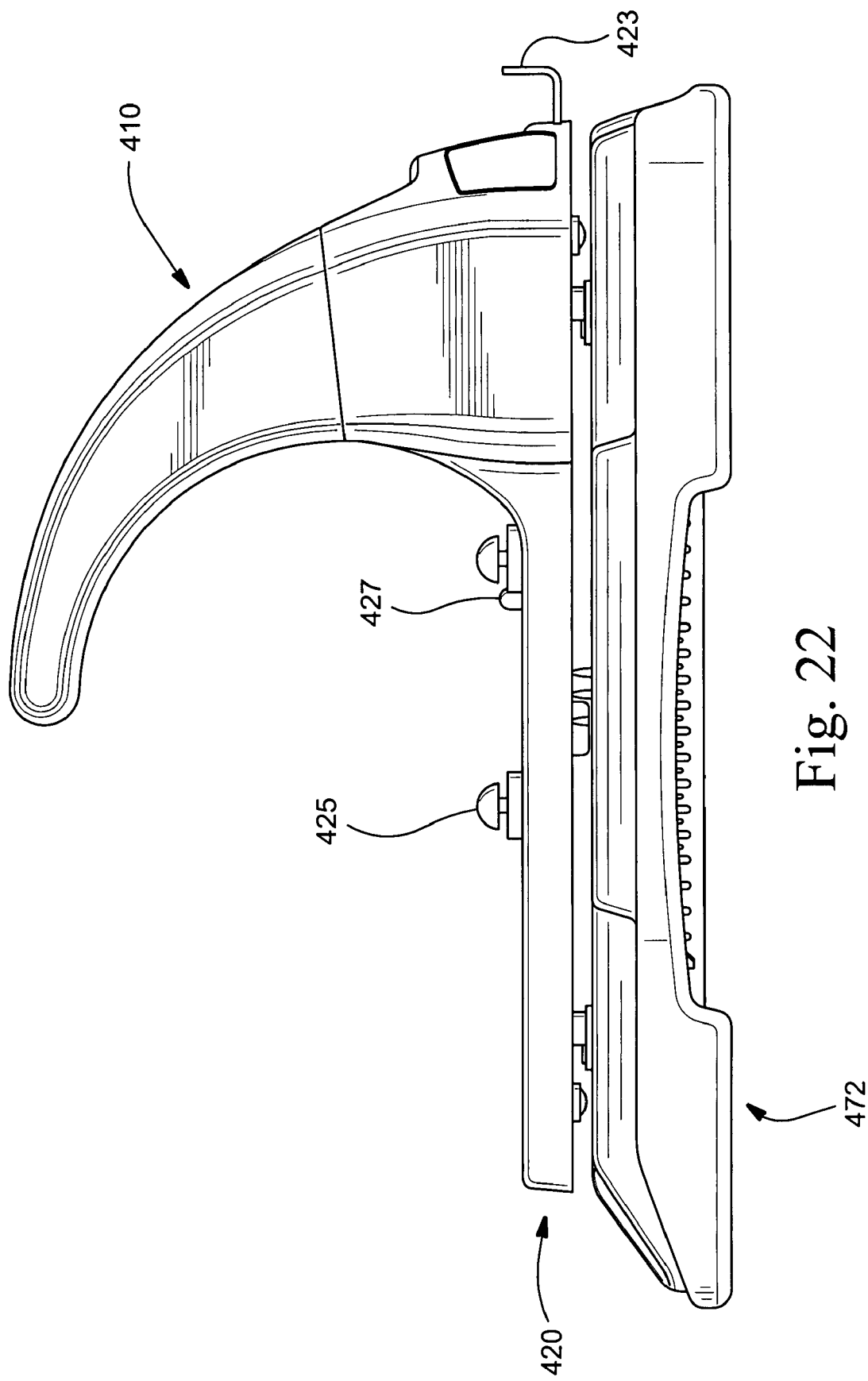
FIG. 22 is a side view of the cradle of FIG. 21 with engaging pins and locking pin.

FIG. 22 shows a side view of the cradle 410 with engaging pins 425 and locking pin 427. From this perspective the engaging pins' 425 mushroom-like shape is visible. Although that was the shape chosen for engagement in this illustrated embodiment, any shape capable of engaging a receiving tab may be used. Also, in this view, the battery 472 is shown attached to the base 420. The battery may be unlocked from the base by means of the locking plate release handle 423.

Figure 23:
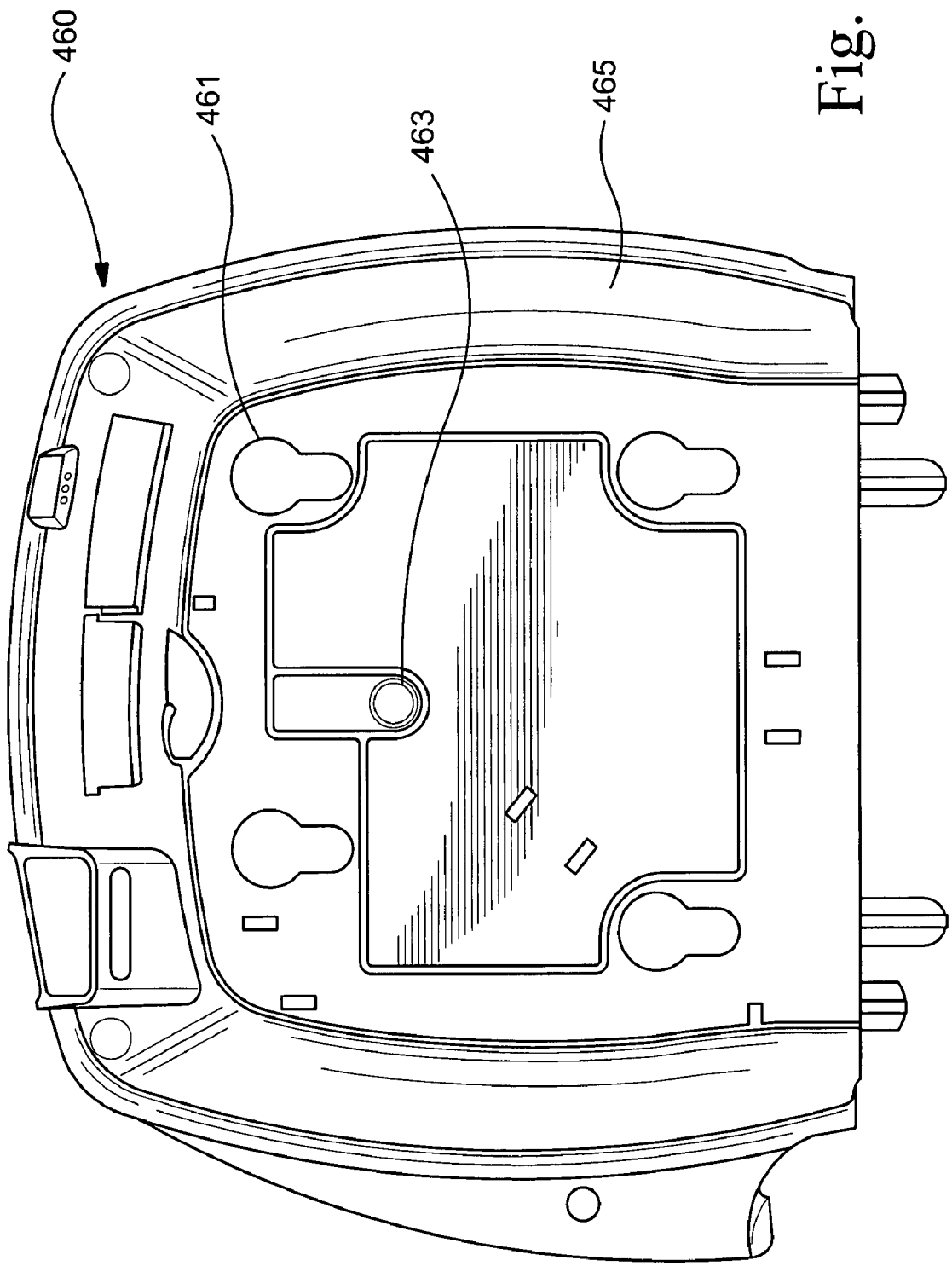
FIG. 23 is a bottom face of a PAP device adapted to engage locking pins provided on a cradle according to an embodiment of the present invention.

FIG. 23 shows a bottom face 465 of a PAP device adapted to engage locking pins provided on a cradle. The PAP device 460 is provided with at least one engagement tab 461 set in the PAP device base 465. The tab or tabs 461 provided in the PAP device base 465 are aligned so as to match up with the alignment of the engaging pins provided on the cradle. The PAP device 460 may then be set into the cradle and the engagement tabs 461 engage the engaging pins and hold the PAP device 460 in place.

Additionally, the PAP device 460 may be provided with a receiving portion 463 for a locking pin provided on the cradle. The locking pin may lock into the receiving portion 463 and provide further support to hold the PAP device 460 in place in the cradle.

Figure 24:
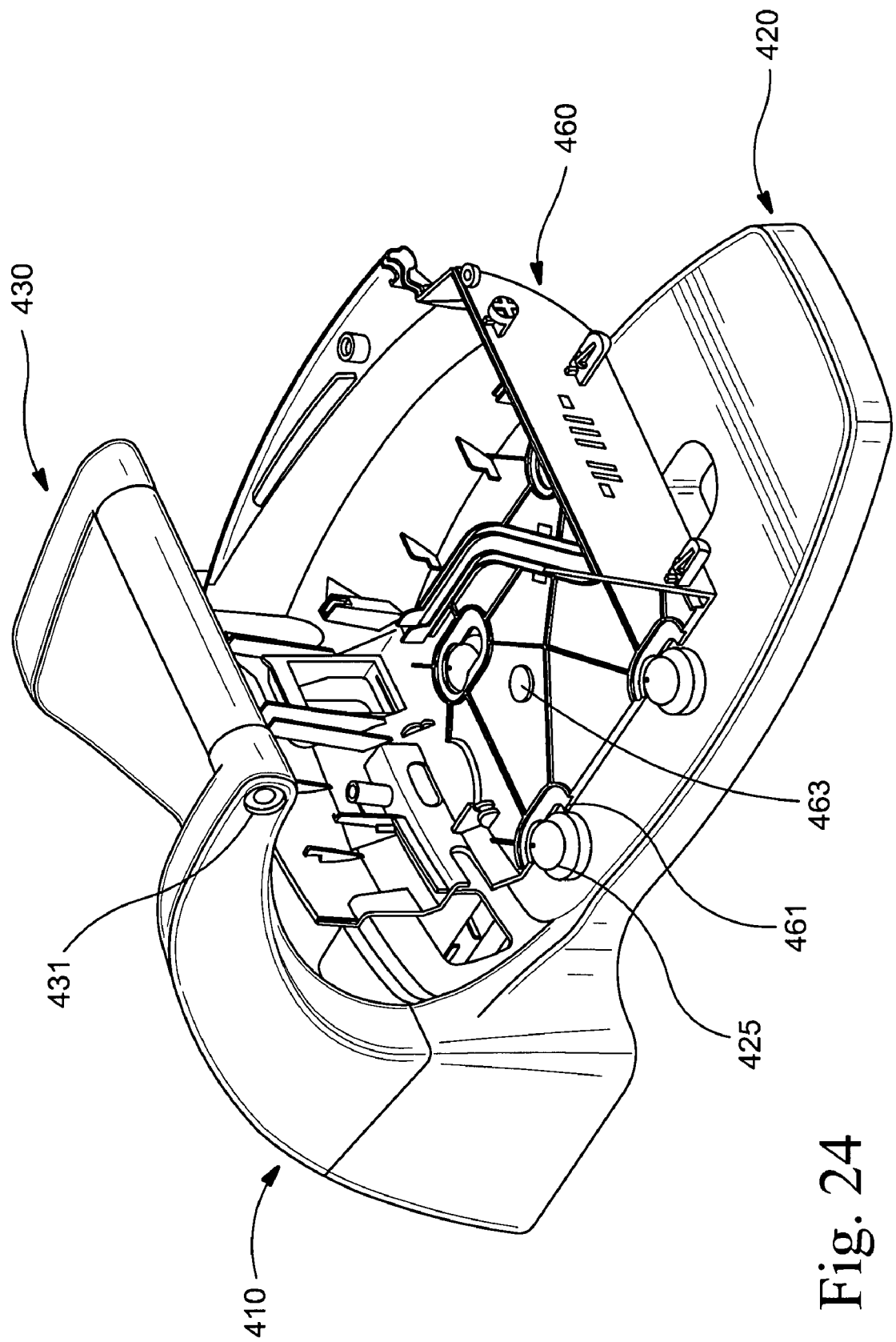
FIG. 24 is a cut-away view of a PAP device in position to be locked to a cradle according to an embodiment of the present invention.

FIG. 24 shows a cut-away view of a PAP device 460 in position to be locked to a cradle 410. The engagement tabs 461 have been placed over the tops of the engaging pins 425. When the PAP device 460 is slid backwards, the engagement tabs 461 will lock onto the engaging pins 425, and a locking pin on the base 420 of the cradle will lock into the receiving portion 463.

Figure 25:
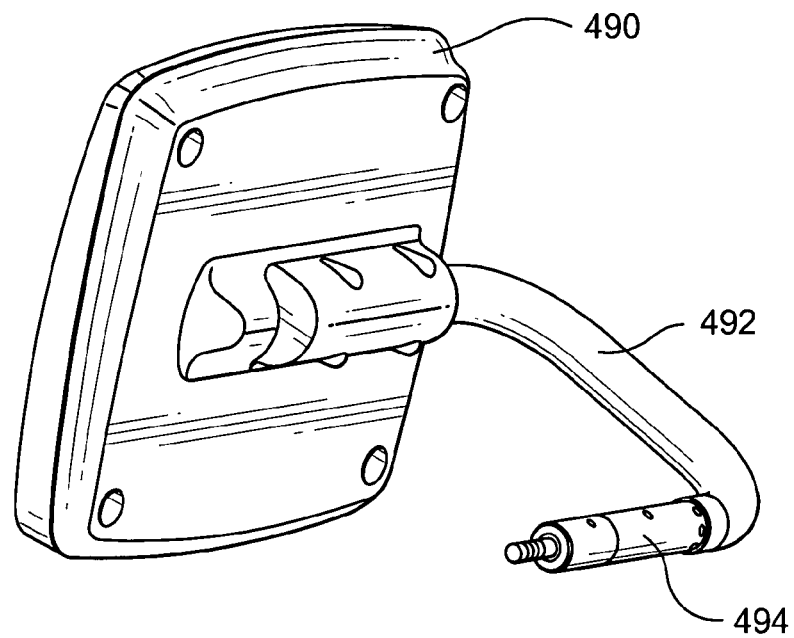
FIG. 25 is a perspective view of a screen outfitted with an electrical and communications connector according to an embodiment of the present invention.

Also shown in this view is another embodiment of a handle, provided with a receiver 431 adapted for receiving an electrical and communications connector e.g. see electrical and communications connector 494 in FIG. 25.

7. Additional Screen Embodiments

FIG. 25 shows a perspective view of a screen 490 outfitted with an electrical and communications connector 494. The screen 490 is attached to an arm 492 and the end of the arm 492 is provided with the electrical and communications connector 494. The screen 490 may be configured to provide any desired display of information. The electrical and communications connector 494 may be adapted to fit into an electrical and communications receptor on the handle of a cradle.

Figure 26:
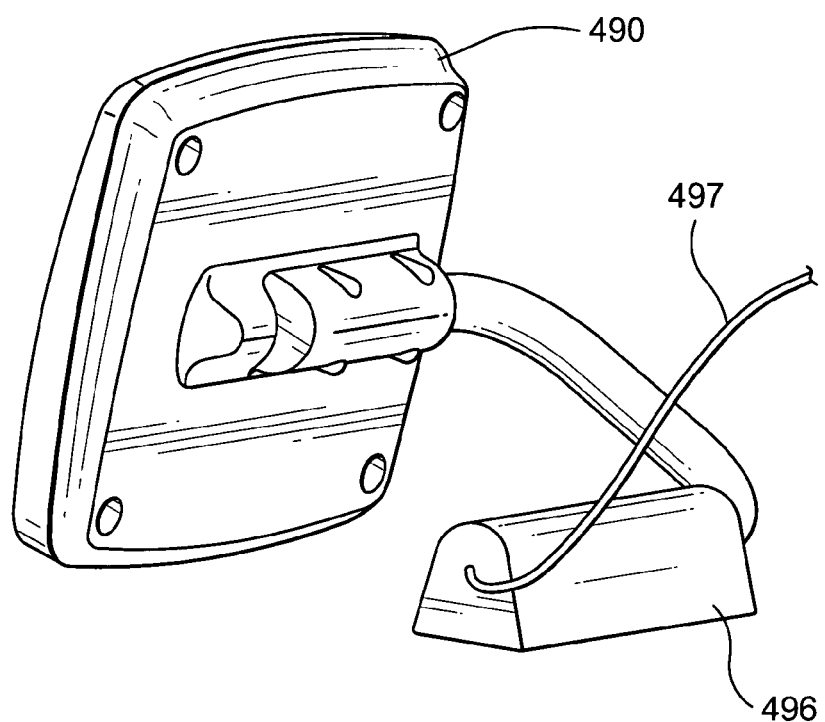
FIG. 26 is a perspective view of the screen of FIG. 25 where the electrical and communications connector has been interfaced with an adapter.

FIG. 26 shows a perspective view of the screen 490 of FIG. 25 where the electrical and communications connector has been interfaced with an adapter 496. The adapter 496 may be provided with a cord 497 which may be connected to the PAP device, allowing the adapter 496 and screen 490 to be moved away from the cradle and viewed without use of the cradle.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A portable cradle for carrying a PAP device of a breathing apparatus, the cradle comprising:
   a base structured to receive the PAP device on a first side; and
   a handle provided on the base,
   wherein the handle is configured to allow the PAP device to be carried when the PAP device is received within the base; and the base is oriented in a substantially horizontal position when the handle is lifted.

2. The portable cradle of claim 1, wherein the first side of the base comprises at least one engageable member structured to receive at least one complementary engageable member disposed on the PAP device.

3. The portable cradle of claim 2, wherein the base further comprises a first locking member adapted to lock into a receiving member disposed on the PAP device.

4. The portable cradle of claim 3, wherein the base further comprises a first lock release member configured to release the first locking member from the first receiving member of the PAP device.

5. The portable cradle of claim 1, further comprising at least one battery module attached to the base.

6. The portable cradle of claim 5, wherein the at least one battery module further comprises at least one removable, rechargeable battery pack.

7. The portable cradle of claim 5, wherein the at least one battery module is disposed between the PAP device and the base.

8. The portable cradle of claim 1, wherein the base is structured to receive at least one battery module on a second side.

9. The portable cradle of claim 8, wherein the second side of the base comprises at least one engageable member structured to receive at least one engageable member located on the battery module.

10. The portable cradle of claim 9, wherein the base further comprises a second locking member adapted to lock the at least one battery engageable member to the base.

11. The portable cradle of claim 10, wherein the base further comprises a second lock release member configured to release the at least one battery engageable member from the second locking member.

12. The portable cradle of claim 1, wherein the cradle further comprises a body portion disposed on the base, the body portion structured to support at least one accessory connected to the PAP device.

13. The portable cradle of claim 12, wherein the body portion comprises at least one opening.

14. The portable cradle of claim 12, wherein the body portion is structured to provide a storage space for at least one communication cord.

15. The portable cradle of claim 1, wherein the handle comprises at least one arm that upwardly extends from the base.

16. The portable cradle of claim 15, wherein the handle further comprises at least one carrying portion disposed at an end of the at least one arm that is opposite the base so that the carrying portion is positioned opposite the base.

17. The portable cradle of claim 15, wherein the at least one arm comprises two arms.

18. The portable cradle of claim 17, wherein the carrying portion is disposed between ends of the two arms that are opposite the base so that the carrying portion is positioned opposite the base.

19. The portable cradle of claim 15 wherein the handle further comprises an electrical and communications receptor.

20. The portable cradle of claim 1, wherein the handle is spaced above the PAP device once the PAP device is loaded into the base.

21. A portable cradle for carrying a PAP device and a battery module of a breathing apparatus, the cradle comprising:
a base structured to receive the battery module; and
a handle provided on the base,
wherein the handle is configured to allow the PAP device to be carried when the PAP device is received within the base; and the PAP device is attached to the base on a side opposite the battery module.

22. The portable cradle of claim 21, wherein the handle comprises at least one arm that upwardly extends from the base.

23. The portable cradle of claim 22, wherein the handle further comprises at least one carrying portion disposed at an end of the at least one arm that is opposite the base so that the carrying portion is positioned opposite the base.

24. The portable cradle of claim 22, wherein the at least one arm comprises two arms.

25. The portable cradle of claim 24, wherein the carrying portion is disposed between ends of the two arms that are opposite the base so that the carrying portion is positioned opposite the base.

26. A portable breathing apparatus assembly, comprising:
a PAP device; and
a cradle having a base that, upon assembly, receives a PAP device on a first side,
wherein the cradle comprises a handle provided to the base,
wherein the handle is configured to be carried when the CPAP device is received in the base, and the PAP device is oriented in a substantially horizontal position when the handle is lifted.

27. The portable breathing apparatus assembly of claim 26, further comprising an oxygen blender connected to the PAP device.

28. The portable breathing apparatus assembly of claim 27, wherein the oxygen blender is physically and pneumatically connected to the PAP device and electrically connected to the cradle.

29. The portable breathing apparatus assembly of claim 26, further comprising a battery module.

30. The portable breathing apparatus of claim 26, wherein the handle is spaced above the PAP device once the PAP device is loaded into the base.

* * * * *